(12) United States Patent
Kool

(10) Patent No.: US 6,479,650 B1
(45) Date of Patent: *Nov. 12, 2002

(54) FLUORESCENT NUCLEOSIDE ANALOGS AND COMBINATORIAL FLUOROPHORE ARRAYS COMPRISING SAME

(75) Inventor: Eric T. Kool, Stanford, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/461,636

(22) Filed: Dec. 14, 1999

(51) Int. Cl.$^7$ ............................................. C07H 15/00
(52) U.S. Cl. ........................ 536/17.4; 536/4.1; 536/18.1
(58) Field of Search ................................ 536/4.1, 18.1, 536/17.4, 24.3

(56) References Cited

U.S. PATENT DOCUMENTS

| | | | |
|---|---|---|---|
| 5,412,088 A | 5/1995 | Jones et al. | |
| 5,652,099 A | 7/1997 | Conrad | |
| 6,140,480 A | * 10/2000 | Kool | ........................ 536/18.1 |

FOREIGN PATENT DOCUMENTS

WO    WO 97/43298    11/1997

OTHER PUBLICATIONS

Fox J.J. et al., "Nucleosides. LXXIII. Ribosyl Analogs of Chloramphenicol", *J. Org. Chem.* 36(26):4113–4116 (1971).

Millican T.A. et al., "Synthesis and Biophysical Studies of Short Oligodeoxynucleotides with Novel Modifications: A Possible Approach to the Problem of Mixed Base Oligodeoxynucleotide Synthesis", *Nucleic Acids Research* 12(19):7435–7453 (1984).

Francois P. et al., "A High Field NMR Study of 2–Deoxyribo–C–Nucleosides", *Nucleosides & Nucleotides* 9(3):379–382 (1990).

Matulic–Adamic J. et al., "Synthesis and Structure of 1–Deoxy–1–Phenyl–β–D–Ribofuranose and Its Incorporation into Oligonucleotides", *J. Org. Chem.* 61(11):3909–3911 (1996).

Luyten I. et al., "The Electronic Nature of the Aglycone Dictates the Drive of the Pseudorotational Equilibrium of the Pentofuranose Moiety in C–Nucleosides", *Nucleosides & Nucleotides* 17(9–11):1605–1611 (1998).

Wichai U. et al., "Disiloxane–Protected 2–Deoxyribonolactone as an Efficient Precursor to 1,2–Dideoxyl–1–β–Aryl–D–Ribofuranoses", *Organic Letters* 1(8):1173–1175 (1999).

Cunningham, R.E., "Fluorescent Labeling of DNA", *Methods of Molecular Biology*, vol. 115: 271–273 (1999).

Royer, C.A., "Fluorescence Spectroscopy", *Methods in Molecular Biology*, vol. 40: 65–89 (1995).

Millar, D.P., "Time–resolved fluorescence spectroscopy", *Current Opinion in Structural Biology*, vol. 6: 637–642 (1996).

Matray, T.J., et al., "Selective and Stable DNA Base Pairing without Hydrogen Bonds", *J. Am. Chem. Soc.*, vol. 120: 6191–6192 (1998).

Barrio, J.R., et al., "Fluorescent Adenosine and Cytidine Derivatives", *Biochemical and Biophysical Research Communications*, vol. 46(2): 597–604 (1972).

Srivastava, S.C., et al., "1, $N^6$–etheno deoxy and ribo adenosine and 3, $N^4$–etheno deoxy and ribo cytidine phosphoramidites. Strongly fluorescent structures for selective introduction in defined sequence DNA and RNA molecules", *Nucleic Acids Research*, vol. 22(7): 1296–1304 (1994).

Ward, D.C., et al., "Fluorescence Studies of Nucleotides and Polynucleotides", *The Journal of Biological Chemistry*, vol. 244(5): 1228–1237 (1969).

Allan, B.W., et al., "Measurement of the Absolute Temporal Coupling between DNA Binding and Base Flipping", *Biochemistry*, vol. 38: 5308–5314 (1999).

Otto, M.R., et al., "Stopped–Flow Fluorescence Study of Precatalytic Primer Strand Base–Unstacking Transitions in the Exonuclease Cleft of Bacteriophage T4 DNA Polymerase", *Biochemistry*, vol. 37: 10156–10163 (1998).

Bujalowski, W., et al., "Structural Characteristics of the Nucleotide–Binding Site of *Escherichia coli* Primary Replicative Helicase DnaB Protein. Studies with Ribose and Base–Modified Fluorescent Nucleotide Analogs", *Biochemistry*, vol. 33: 4682–4694 (1994).

(List continued on next page.)

*Primary Examiner*—Elli Peselev
(74) *Attorney, Agent, or Firm*—Scully, Scott, Murphy, Presser

(57) ABSTRACT

The present invention provides fluorescent nucleoside analogs which comprise a fluorescent cyclic compound joined to a carbon of a sugar molecule such as pentose, hexose, ribose or deoxyribose or analogs thereof in either an α or β configuration. The subject compounds are useful as probes in the study of the structure and dynamics of nucleic acids and their complexes with proteins. In addition, the subject compounds are useful in any technique which uses labeled oligonucleotides for detection. Non-fluorescent spacer molecules in which a cyclohexane, cyclohexene, decalin, or benzene is joined to a carbon of a sugar moiety such as pentose, hexose, ribose or deoxyribose are also provided. Also provided are the 5' dimethoxytrityl-3'-O-phosphoramidite derivatives, suitable for incorporation into oligonucleotides by automated synthesizers. Combinatorial fluorophore array (CFA) libraries comprising oligomers of the subject nucleoside analogs attached to one or more solid supports are also provided as are methods of selecting fluorophores from the CFA libraries. The present invention also provides oligonucleotide analogs comprising one or more of the subject nucleoside analogs in place of a DNA or RNA base.

48 Claims, 5 Drawing Sheets

OTHER PUBLICATIONS

Ren, R.X.F., et al., "Naphthalene, Phenanthrene, and Pyrene as DNA Base Analogues: Synthesis, Structure, and Fluorescence in DNA", *J. Am. Chem. Soc.*, vol. 118: 7671–7678 (1996).

Moran, S., et al., "Non–hydrogen bonding 'terminator' mucleosides increase the 3'end homogeneity of enzymatic RNA and DNA synthesis", *Nucleic Acids Research*, vol. 24(11): 2044–2052 (1996).

Coleman, R.S., et al., "Synthesis of a novel Coumarin C–Riboside as a Photophysical Probe of Oligonucleotide Dynamics", *J. Org. Chem.*, vol. 63: 5700–5703 (1998).

Erzberger, J.P., et al., "Elements in abasic site recognition by the major human and Escherichia coli apurinic/apyrimidinic endonucleases", *Nucleic Acids Research*, vol. 26(11): 2771–2778 (1998).

Paris, P.L., et al., "Probing DNA sequences in solution with a monomer–excimer fluorescence color change", *Nucleic Acids Research*, vol. 26(16): 3789–3793 (1998).

Guckian, K.M., et al., "Experimental Measurement of Aromatic Stacking Affinities in the Context of Duplex DNA", *J. Am. Chem. Soc.*, vol. 118: 8182–8183 (1996).

Matray, T.J., et al., "A specific partner for abasic damage in DNA", *Nature*, vol. 399: 704–708 (1999).

Chaudhuri, N.C., et al., "An Efficient for the Synthesis of Aromatic C–Nucleosides", *Tetrahedron Letters*, vol. 11: 1795–1798 (1995).

Chaudhuri, N.C., et al., "C–Nucleosides Derived from Simple Aromatic Hydrocarbons", *Synlett*, 341–347 (1997).

Morvan, F., et al., "α–Oligonucleotides: a unique class of modified chimeric mucleic acids", *Anti–Cancer Drug Design*, vol. 6: 521–529 (1991).

Manoharan, M., et al., "Base–Sequence Dependence of Emission Lifetimes for DNA Oligomers and Duplexes Covalently Labeled with Pyrene: Relative Electron–Transfer Quenching Efficiencies of A, G, C, and T Nucleosides toward Pyrene", *J. Phys. Chem.*, vol. 99: 17461–17472 (1995).

Mohanakrishnan, A.K., et al., "Studies in the Dithienylbenzo [c] thiophene Series", *J. Org. Chem.*, vol. 63: 3105–3112 (1998).

McKillop, A., et al., "Thallium in Organic Synthesis. XXV. Electrophilic Aromatic Bromination Using Bromine and Thallium(III) Acetate$^{1-3}$", *J. Org. Chem.*, vol. 37(1): 88–92 (1972).

Rossi, R., et al., "Selective and Efficient Synthesis of Phototoxic 2,2':5',2"–Terthiophene Derivatives Bearing A Functional Substituent In The 3'– Or The 5–Position", *Tetrahedron*, vol. 47(39): 8443–8460 (1991).

Bäuerle, P., et al., "Selective Synthesis of α–Substituted Oligothiophenes", *Synthesis*, 1099–1103 (1993).

Cardona, L., et al., "Synthesis of Natural Polyhydroxystilbenes", *Tetrahedron*, vol. 42(10) 2725–2730 (1986).

Ndebeka, G., et al., "Alkoxide Variation in Complex Base–Promoted Syn Dehydrohalogenations", *J. Org. Chem.*, vol. 45: 5394–5396 (1980).

Hoffer, M., "α–Thymidin", *Chem. Ber.*, vol. 93: 2777–2781 (1960).

Garcia, P., et al., "Effect of End Substitution on Electrochemical and Optical Properties of Oligothiophenes", *J. Phys. Chem.*, vol. 97: 513–516 (1993).

Telser, J., et al., "Synthesis and Characterization of DNA Oligmers and Duplexes Containing Covalently Attached Molecular Labels: Comparison of Biotin, Fluorescein, and pyrene Labels by Thermodynamic and Optical Spectroscopic Measurements", *J. Am. Chem. Soc.*, vol. 111: 6966–6976 (1989).

Lewis, F.D., et al., "Hybrid Oligonucleotides Containing Stilbene Units. Excimer Fluorescene and Photodimerization", *J. Am. Chem. Soc.*, vol. 117: 8785–8792 (1995).

Simpson, D.J., et al., "A Mechanism–Based Flurogenic Probe for the Cytochrome P–450 Cholesterol Side Chain Cleavage Enzyme", *J. Org. Chem.*, vol. 56: 5391–5396 (1991).

Demas, J.N., et al., "The Measurement of Photoluminescence Quantum Yields. A Review", *The Journal of Physical Chemistry*, vol. 75(8): 991–1024 (1971).

Olmstead III, J., "Calorimetric Determinations of Absolute Fluorescence Quantum Yields", *The Journal of Physical Chemistry*, vol. 83: 2581–2584 (1979).

Lundblad, J.R., et al., "Fluorescence Polarization Analysis of Protein–DNA and Protein–Protein Interactions", *Molecular Endocrinology*, vol. 10: 607–612 (1996).

Beaucage, S.L., et al., "The Functionalization of Oligonucleotides Via phosphoramidite Derivatives", *Tetrahedron*, vol. 49(10): 1925–1963 (1993).

Wu, P., et al., "Resonance Energy Transfer: Methods and Applications", *Analytical Biochemistry*, vol. 218: 1–13 (1994).

Adhya, S., "RNA Polymerase and Associated Factors", *Methods in Enzymology*, vol. 274: 492–503 (1996).

Sauer, K., "Biochemical Spectroscopy", *Methods in Enzymology*, vol. 246: 334–363 (1995).

Coleman R. et al., "Synthesis of a Novel Coumarin C–Riboside as a Photophysical Probe of Oligonucleotide Dynamics", *J. Org. Chem.*, 63: 5700–5703 (1998).

Gasparro, F. et al., "The Effects of Gilvocarcin V and Ultraviolet Radiation on pBR322 DNA Lymphocytes", *Chem. Biol. Interactions*, 67: 255–265 (1988).

Strassler, C. et al., "Novel Nucleoside Analogues with Fluorophores Replacing the DNA Base", *Helvetica–Chimica Acta*, 82: 2160–2171 (1999).

* cited by examiner

FLUORESCENT NUCLEOSIDE ANALOGS AND COMBINATORIAL FLUOROPHORE ARRAYS COMPRISING SAME

BACKGROUND OF THE INVENTION

Fluorescence methods are extremely widespread in chemistry and biology. The methods give useful information on structure, distance, orientation, complexation, and location for biomolecules [1]. In addition, time-resolved methods are increasingly used in measurements of dynamics and kinetics [2]. As a result, many strategies for fluorescence labeling of biomolecules, such as nucleic acids, have been developed [3]. In the case of DNA, one of the most convenient and useful methods for fluorescence labeling is to add a fluorescent moiety during the DNA synthesis itself. Addition of the fluorescent moiety during DNA synthesis avoids the extra steps required for post-synthesis labeling and purification. The majority of labels commonly used during DNA synthesis are attached to the DNA by tethers that are often 5 to 11 atoms long. These flexible tethers can at times be problematic, since they allow the dye to tumble independently of the DNA and -make the location of the dye difficult to determine precisely [4]. There are very few examples of dye conjugates that hold the dye close to the DNA, thus avoiding these problems. Among the known dyes of this class are ethenodeoxyadenosine [5] and 2-aminopurinedeoxyriboside [6]. These latter two compounds have modified DNA bases that are themselves fluorescent, and have found much use as probes of enzymatic activities such as DNA synthesis, editing, and repair [7–9].

The present invention provides fluorescent labels for nucleic acids which, rather than modifying an existing nucleic acid base, replace one or more DNA or RNA bases with a fluorescent cyclic compound. Since the replacement fluorescent cyclic compound is also a flat cyclic structure, only small perturbations to the overall nucleic acid structure occur upon its use. The fluorescent label may be thought of as a nucleoside analog in which a known fluorescent cyclic compound is joined to a carbon atom of a sugar moiety. The subject nucleoside analogs allow for close interaction, including stacking, with a neighboring RNA or DNA helix. There are many known cyclic fluorophores which may be joined to a carbon atom of a sugar moiety to form the nucleoside analogs of the present invention. Many of the known cyclic fluorophores have high quantum yields with varied excitation and emission characteristics. Moreover, their lack of functional groups makes them relatively simple to work with in preparing conjugates.

The literature has reported incorporation of 4-methylindole, naphthalene, phenanthrene, and pyrene fluorophores at the C1-position of deoxyribose [10,11]. In a similar strategy, the substitution of a coumarin dye at the C1 position of deoxyribose has also been reported[12]. The methylindole derivative has recently found use as a fluorescent reporter of DNA repair activities [13]. In addition, the C1α pyrene derivative has been shown to be useful in DNA diagnostics strategies, where it efficiently forms excimers with neighboring pyrene labels [14]. The C1β pyrene derivative stabilizes DNA helices markedly (due to its low polarity) [15,16], and can be enzymatically incorporated into the DNA helix [17]. Thus, this new nucleic acid labeling strategy has many useful applications.

The present invention provides nucleoside analogs with improved fluorescence characteristics, increasing the range of emission wavelengths over those previously studied. The subject nucleoside analogs are more generally useful in biophysical and diagnostics applications. These new compounds significantly broaden the range of fluorescence properties available for automated incorporation into DNA.

Although not all interactions between fluorophores are well understood, it is clear that there is more than one type of interaction between light-absorbing molecules. One useful class of interaction is Forster energy transfer, also called fluorescence resonance energy transfer, or FRET. In this interaction, fluorescence emission is transferred from a donor to an acceptor fluorophore. The extent of transfer depends on distance and on overlap in emission and absorption of donor and acceptor. FRET can occur over relatively long distances (tens of Angstroms). A second form of energy transfer is exciplex formation, which involves bonding between an excited-state fluorophore and a neighboring ground-state fluorophore. This results in a long red shift to fluorescence. Exciplexes can form only between molecules in direct contact or very nearly so. Exciplexes between two of the same molecules are known as excimers. Another class of interaction involving a fluorophore is quenching, in which a molecule causes the quantum yield of nearby fluorescent molecule to be lowered.

These forms of energy transfer are not well explored in systems where more than two chromophores are involved. FRET is now well known between pairs of well understood and widely used dyes, such as fluorescein, rhodamine, acridine, or cyanine dyes. Heretofore, FRET between more than two dyes has been unknown and unexplored. Similarly, while interactions between a few excimer-forming dyes such as stilbene and pyrene are known, exciplex interactions have not been widely explored for combinations of dyes. Little is known about the interactions among more than two fluorophores. Reasons for the dearth of study in this area include lack of available methods for assembling fluorophores in a regular designed fashion. The study of more complex molecules could entail an inordinate number of combinations even where only a few dyes are used. Assembling even a small fraction of these possibilities for study heretofore has been a daunting task. Even if carried out, many combinations of fluorophores lead to undesirable properties such as quenching. For example, placing two fluorescein labels close together results in very weak fluorescence emission.

The present invention allows for the generation of nucleoside analogs and nucleic acids incorporating the subject nucleoside analogs resulting in many types of fluorescence properties such as emission wavelength, emission intensity, and Stokes shift. Combinatorial arrays of fluorophores built on a nucleic acid backbone may be generated and screened for fluorophores having useful fluorescent properties such as high molar absorptivities which leads to high localized fluorescense intensities. Fluorophores providing multiple energy transfer, leading to very large Stokes shifts may also be identified from a library of combinatorial arrays. Large Stokes shifts are useful in avoiding background interference in fluorescence. FRET and exciplex forms of energy transfer usually lead to large changes in emission wavelength, resulting in many possible colors for ease of detection.

SUMMARY OF THE INVENTION

The present invention provides nucleoside analogs comprising a fluorescent cyclic compound joined to a carbon of a pentose, hexose, ribose or deoxyribose sugar moiety in either an α or β configuration. In a preferred embodiment, the fluorescent cyclic compound is joined to the C1 position of the sugar moiety.

Examples of fluorescent cyclic compounds which may be joined to the sugar moiety include oligomers of varying length selected from the group consisting of oligothiophene, oligobenzothiophene, oligo(phenylene vinylene), and oligo(phenylene acetylene). Preferably, an oligomer has a length of from 1 to 16. Terthiophene and sexithiophene are examples of oligothiophenes useful as cyclic compounds in the nucleoside analogs of the present invention.

Benzoterthiophene and terbenzothiophene are examples of oligobenzothiophenes useful as fluorescent cyclic compounds joined to a sugar moiety. Dimethylamino stilbene and styrylstilbene are examples of oligo(phenylene vinylenes) useful as fluorescent cyclic compounds joined to carbon of a sugar moiety.

Diphenylacetylene and phenyl (ethynyl) diphenylacetylene are examples of oligo(phenylene acetylenes) useful as fluorescent cyclic compounds joined to a carbon of sugar moiety.

Other fluorescent cyclic compounds useful as fluorescent cyclic compounds joined to a carbon of a sugar moiety include p-terphenyl, perylene, azobenzene, phenazine, napthalene, phenanthroline, acridine, thioxanthrene, chrysene, rubrene, coronene, cyanine, perylene imide, and perylene amide.

Also provided are nucleoside analogs comprising a non-fluorescent cyclic compound joined to a carbon of a pentose, hexose, ribose or deoxyribose sugar moiety wherein the cyclic compound is cyclohexane, cyclohexene, decalin, benzene or dimethylamino benzene.

The nucleoside analogs of the present invention may be derivatized at an available carbon position with a substituent selected from the group consisting of methoxy, ethoxy, alkoxy, alkyl, dimethylamino, diethylamino, nitro, methyl, cyano, carboxy, fluoro, chloro, bromo, iodo and amino.

The present invention also provides nucleic acid molecules comprising at least one subject nucleoside analog. Oligomers comprising the subject nucleoside analogs are also provided.

Also in accordance with the present invention, there are provided phosphoramidite derivatives of the subject nucleoside analogs wherein the phosphoramidite is joined to the sugar moiety at the 3' position. Examples of phosphoramidite derivatives include N,N-diisopropyl-O-cyanoethyl phosphoramidite or O-methyl-phosphoramidite derivatized at the 3' alcohol of the nucleoside analog.

The present invention also provides nucleoside 5'-3'-paratoluoyl diesters derivatized at the C-1 atom of a sugar moiety with a fluorescent cyclic compound.

Methods of synthesizing the subject nucleoside analogs are also provided. The methods comprise the steps of coupling an organocadmium or organozinc derivative of a fluorescent cyclic compound to a carbon of Hoffer's α-chlorosugar and removing the protecting groups with a methanolic base.

Also provided are methods of synthesizing a phosphoramidite derivative of a subject nucleoside analog. The method comprises:coupling an organocadmium or organozinc derivative of a fluorescent cyclic compound to a carbon atom of Hoffer's a-chlorosugar, removing the protecting groups with a methanolic base; tritilating the 5'-OH with dimeoxytritylchloride in the presence of a base; and phosphytilating the 3'-OH with a phosphytilating agent.

In addition, the present invention provides a method of preparing a fluorescently labeled nucleic acid molecule which comprises incorporating a subject nucleoside analog into an RNA or DNA molecule under conditions sufficient to incorporate said nucleoside.

A method of detecting a target nucleic acid in a sample to be tested is also provided. The method comprises contacting the target nucleic acid with a nucleic acid probe comprising at least one subject nucleoside analog for a time and under conditions sufficient to permit hybridization between the target and the probe and then detecting said hybridization.

Also provided by the present invention are combinatorial fluorophore array (CFA) libraries which comprise multiple solid supports or multiple locations on a solid support, each support or location having attached thereto an oligomer comprising the subject fluorescent nucleoside analogs. A combinatorial fluorophore array (CFA) library may also comprise one or more unlabeled nucleosides wherein the one or more unlabeled nucleosides are positioned 5' or 3' to the oligomer of fluorescent nucleoside analogs or interspaced between the fluorescent nucleoside analogs. In addition, a CFA library may further comprise one or more non-fluorescent nucleotide analogs selected from the group consisting of cyclohexene-2-deoxyriboside, cyclohexane-2-deoxyriboside, decalin-2-deoxyriboside, and benzene-2-deoxyriboside wherein said one or more non-fluorescent nucleotide analogs is interspaced between the flourescent nucleotide analogs or between the fluorescent nucleoside analogs and the and non-labeled nucleosides.

The present invention also provides a method of selecting a fluorophore suitable for use in labeling a nucleic acid molecule which comprises constructing a subject combinatorial fluorophore array library and selecting a fluorophore emitting the most intense fluorescence or emitting a specific wavelength of light.

Also provided is a method of identifying a fluorophore emitting a large Stokes shifts which comprises constructing a subject combinatorial fluorophore array library, exciting the library at short wavelength, and selecting a fluorophore which emits light at a much longer wavelength.

A method of identifying a fluorophore involved in energy transfer is also provided. The method comprises constructing a subject combinatorial fluorophore array library, hybridizing a nucleic acid comprising a donor or acceptor dye to a nucleic acid sequence in the CFA library and correlating any change in color exhibited by the hybridized molecules with energy transfer. Members of the library which give greater changes in acceptor emission intensity are most efficient at energy transfer.

A method for identifying a fluorophore sequence that changes its emission wavelength or intensity on binding an analyte is also provided. The method comprises constructing a subject combinatorial fluorophore array library, incorporating an analyte affinity molecule, allowing an analyte solution to contact the library, and selecting library members that change emission intensity or wavelength on binding of the analyte molecule.

The present invention also provides oligonucleotide analogs comprising one or more of the subject nucleoside analogs in place of a DNA or RNA base. Further, the subject oligonucleotide analogs may comprise a modification to the sugar-phosphate backbone such as that found in phosphorothioate DNA, 2'-O-methyl RNA, phosphoramidite DNA, 2'fluoro DNA, peptide nucleic acid (PNA) or alpha DNA.

Figure 2:
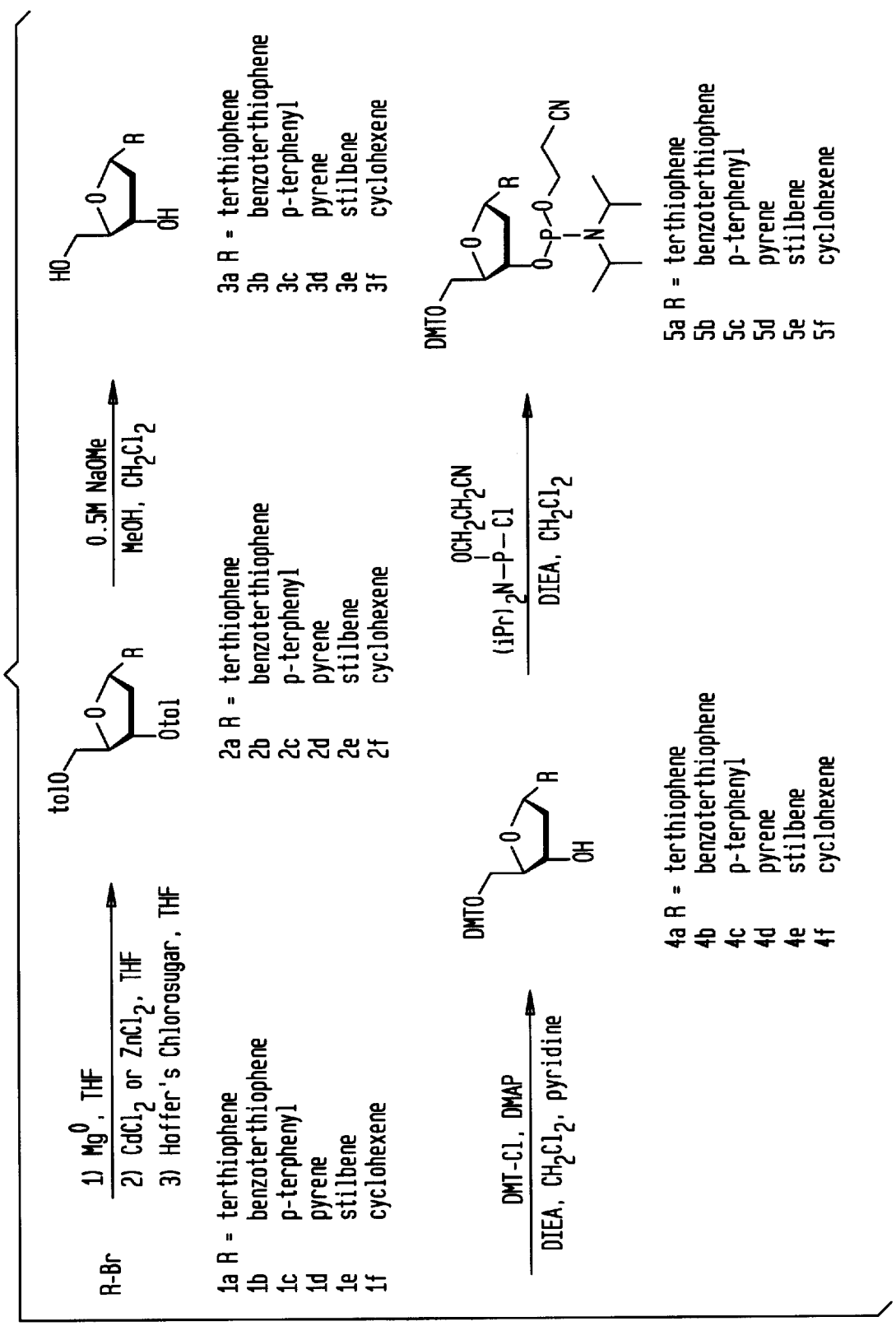

FIG. 2 shows the preparation of C-nucleosides by cadmium- or zinc-mediated reaction of Grignard derivatives of cyclic compounds with Hoffer's chlorosugar. 2a through 2f represent the nucleoside 5'-3'-paratoluoyl diester derivatized at the C-1 atom of a sugar moiety with terthiophene (2a), benzoterthiophene (2b), p-terphenyl (2c), pyrene (2d), stilbene (2e) or cyclohexene (2f).

Figure 3:
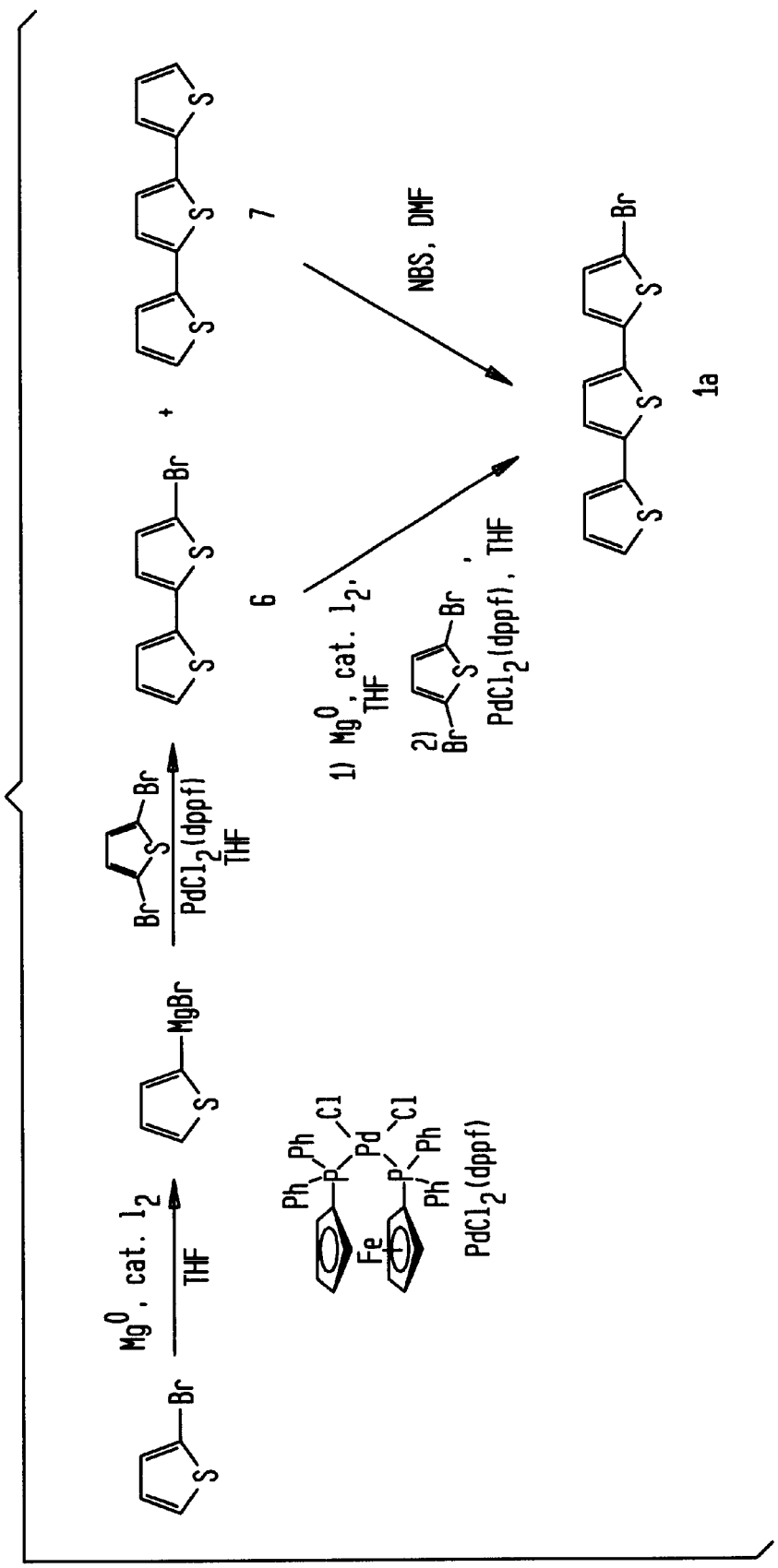

FIG. 3 shows the synthesis of 5-bromo-2,2':5',2"-terthiophene.

Figure 1:
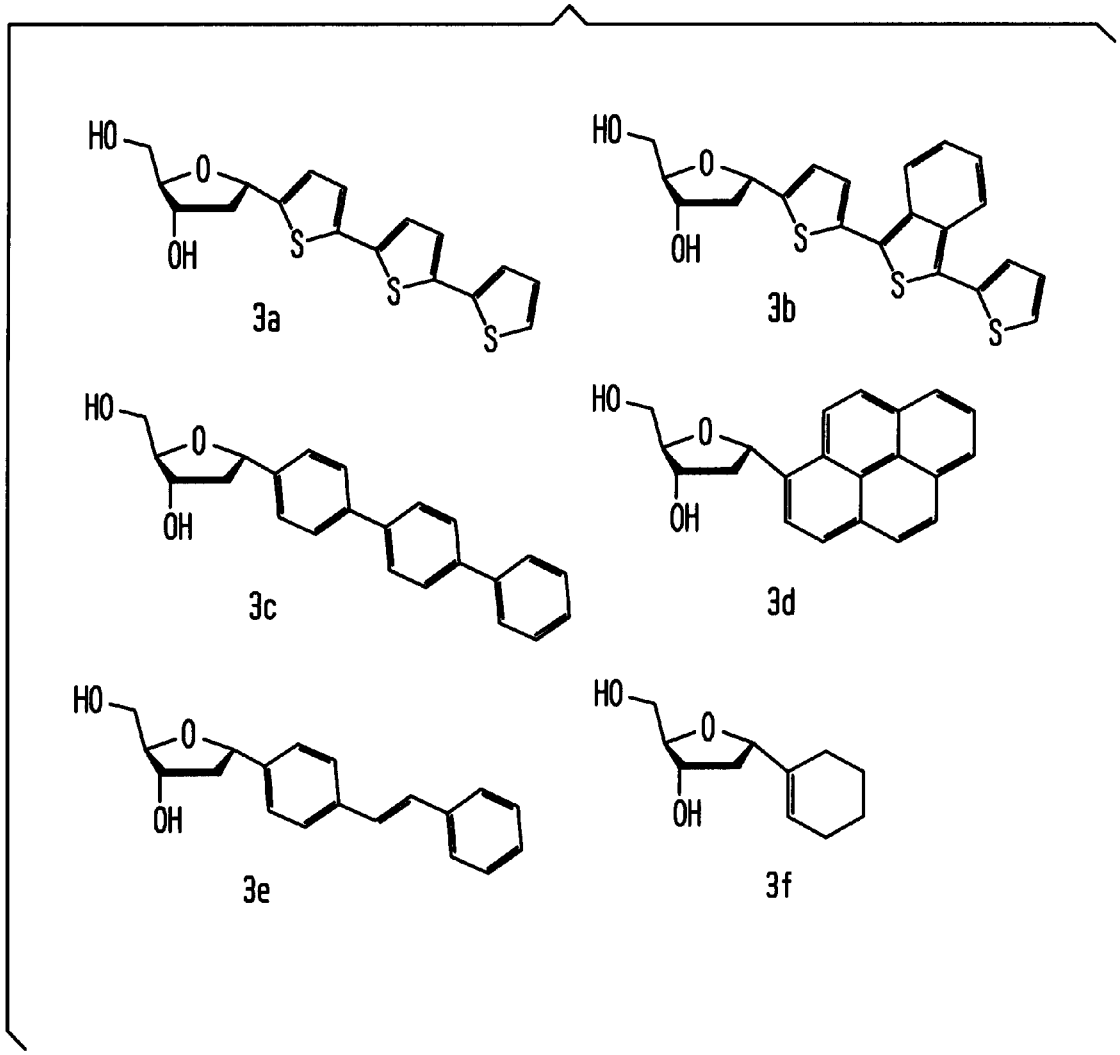
FIG. 1 shows the chemical structures of the nucleoside analogs terthiophene-2-deoxyriboside (3a), benzoterthiophene-2-deoxyriboside (3b), p-terphenyl-2- deoxyriboside (3c), pyrene-2-deoxyriboside (3d), stilbene-2-deoxyriboside (3e), cyclohexene-2-deoxyriboside (3f).
Figure 4:
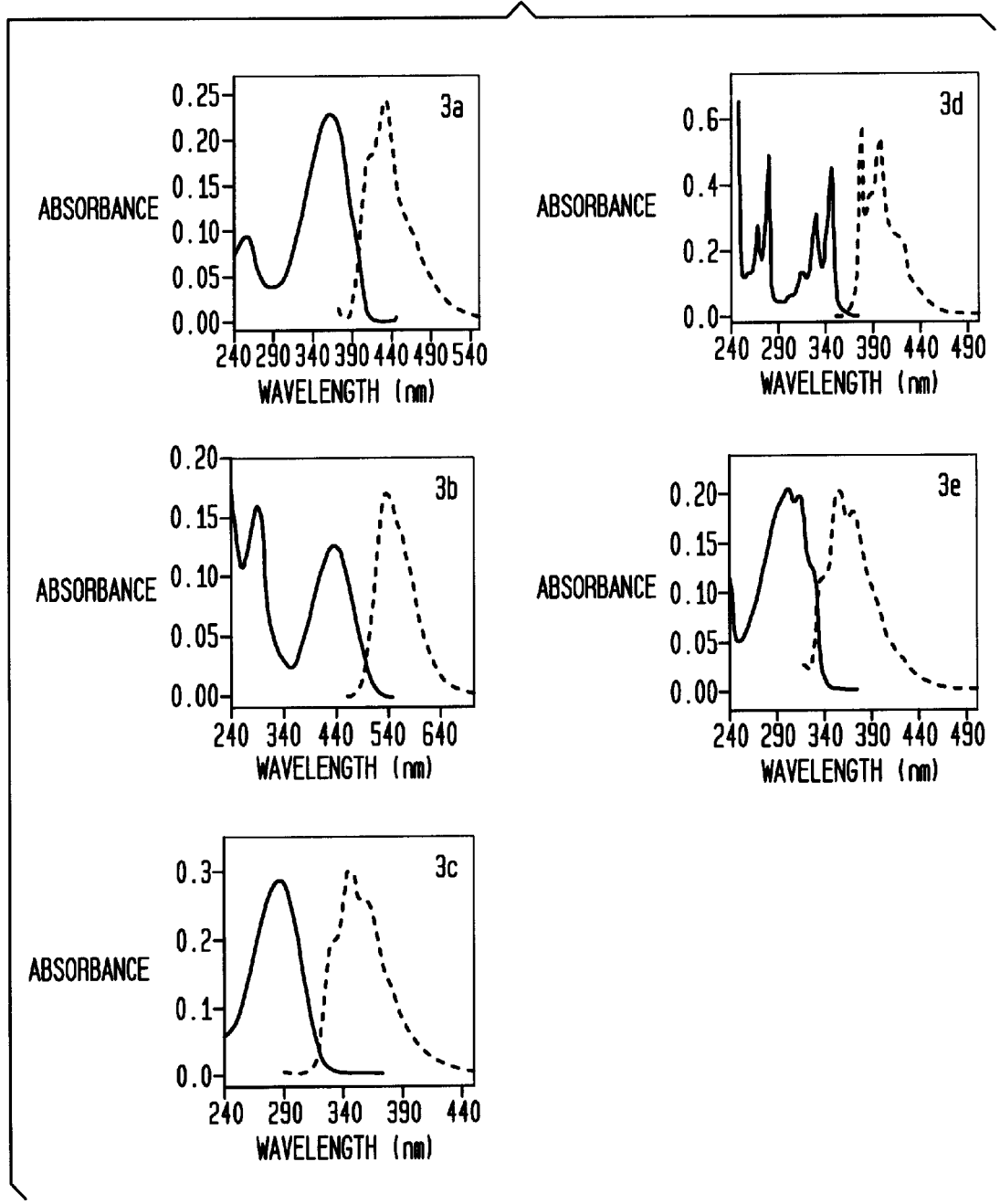

FIG. 4 shows the absorption and normalized emission spectra of free nucleosides 3a–3e of FIG. 1 at 10 $\mu$M concentration in methanol. Solid lines show absorption spectra; dashed lines show normalized emission spectra (arbitrary intensity units), with excitation at the absorption maxima.

Figure 5:
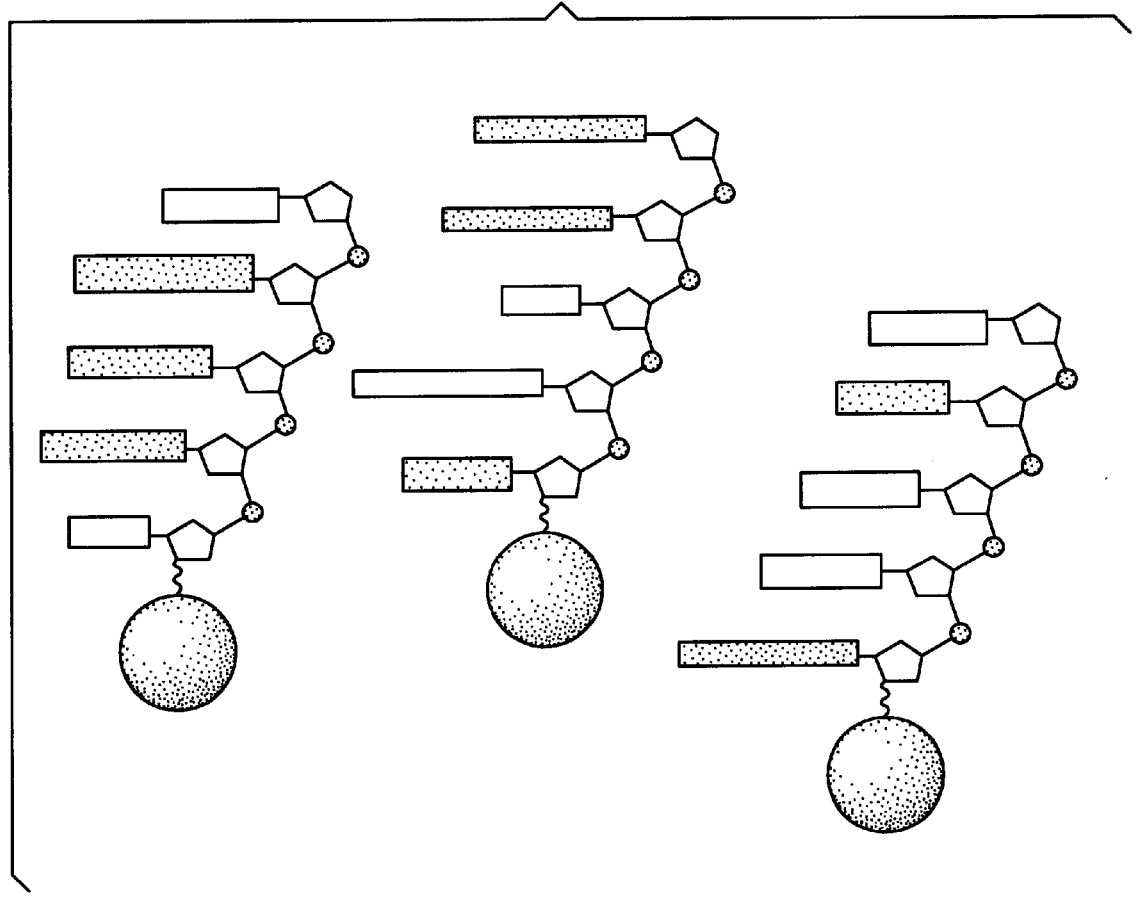

FIG. 5 illustrates three members of a combinatorial fluorophore array (CFA) library. Large dark circles represent solid supports. Small dark circles represent phosphate groups on a nucleic acid molecule of five nucleosides. The different sized and differently shaded rectangular shapes attached to the sugar moieties represent varied cyclic fluorophores.

DETAILED DESCRIPTION OF THE INVENTION

The present invention provides fluorescent labels for nucleic acids which, rather than modifying an existing nucleic acid base, replace one or more DNA or RNA bases with a fluorescent cyclic compound. In accordance with the present invention, there are provided fluorescent nucleoside and nucleotide analogs comprising a fluorescent cyclic compound attached to a carbon of a sugar moiety. The sugar moiety may include, for example, pentose, hexose, ribose, or deoxyribose. In a preferred embodiment, the fluorescent cyclic compound is attached to the C1 position of the sugar moiety. The fluorescent cyclic compound attached to the sugar moiety may include such molecules as oligothiophenes of varying length, oligobenzothiophenes, oligo (phenylene vinylenes), p-terphenyl, perylene, dimethylamino benzene, oligo(phenylene acetylenes) of varying length, azobenzene, phenazine, napthalene, phenanthroline, acridine, thioxanthrene, chrysene, rubrene, coronene, cyanines, perylene imide and perylene amide. Due to the location of the fluorescent cyclic compound on the sugar moiety, the nucleoside analogs of the present invention act as DNA or RNA base analogs. The subject nucleoside and nucleotide analogs stack neatly in an RNA or DNA helix. As used herein, "nucleoside" also encompasses "nucleotide" which is a phosphate ester of a nucleoside. Thus, any reference herein to "nucleoside" or "nucleoside analog" is also meant to include "nucleotide" or "nucleotide analog". As used herein "nucleoside" is also meant to include nucleotide triphosphates.

In addition, the present invention provides a non-fluorescent nucleoside analog having a cyclic compound such as cyclohexane, cyclohexene, decalin, or benzene joined to a carbon atom of a sugar molecule. In a preferred embodiment, the cyclic compound is joined to the C-1 position of a sugar moiety. In another preferred embodiment, the sugar molecule is pentose, hexose, ribose or deoxyribose. Such a nucleoside analog is useful as a non-fluorescent spacer which may be inserted between the subject fluorescent nucleoside analogs and unlabeled nucleic acid bases. Insertion of the non-fluorescent nucleoside in a nucleic acid molecule limits quenching which may occur between the subject fluorophores.

Examples of oligothiophenes of varying length useful as a fluorescent cyclic compound attached to a sugar moiety include terthiophene and sexithiophene. Examples of an oligobenzothiophene useful as a fluorescent cyclic compound attached to a sugar moiety include benzoterthiophene and terbenzothiophene. Dimethylamino stilbene and styryl-stilbene are examples of oligo(phenylene vinylenes) useful as fluorescent cyclic compound attached to a sugar moiety. Examples of oligo(phenylene acetylenes) of varying length useful as a fluorescent cyclic compound attached to a sugar moiety include diphenylacetylene and phenylethynyl (diphenylacetylene). In those particular cases where the polycyclic hydrocarbon is an oligomer, e.g., oligothiophene or oligo(phenylene acetylene), oligomer lengths from about one to about sixteen are contemplated.

In accordance with the present invention, a subject nucleoside analog may be substituted at various positions on its ring structure with one or more alkoxy, alkylamino, dialkylamino, alkyl, alkenyl, alkynyl, hydroxy, or halide groups. Examples include but are not limited to methoxy, ethoxy, dimethylamino, diethylamino, nitro, methyl, cyano, carboxy, fluoro, chloro, bromo, iodo, or amino groups.

A fluorescent cyclic compound is attached at any available position on its ring structure to the sugar moiety by a carbon-carbon bond in a subject fluorescent nucleoside analog. Both alpha and beta anomers of the subject nucleosides are contemplated by the present invention. Similarly, a non-fluorescent cyclic compound is attached at any available position on its ring structure to a sugar moiety by a carbon-carbon bond in a subject non-fluorescent nucleoside analog.

In one embodiment of the invention, an oligothiophene-derivatized nucleoside has the following general structure:

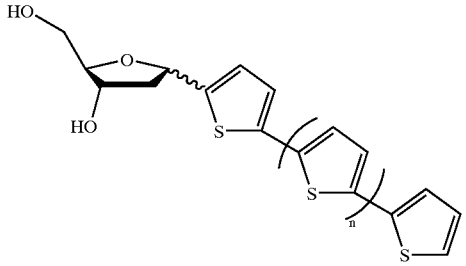

In another embodiment of the invention, an oligothiophene-derivatized nucleoside is terthiophene-2-deoxyriboside, having the following structure:

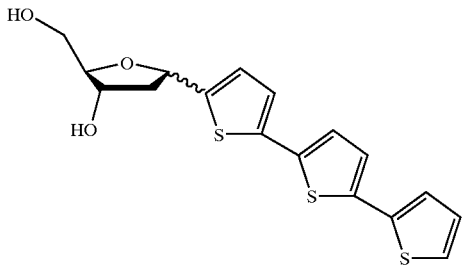

In another embodiment of the invention, an oligothiophene-derivatized nucleoside is a sexithiophene-2-deoxyriboside, having the following structure:

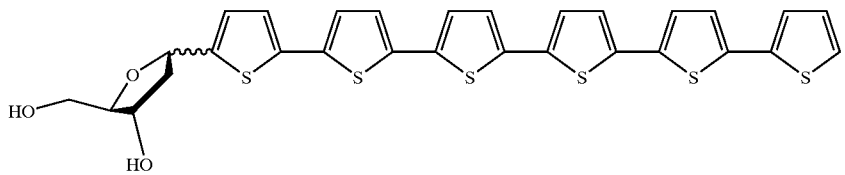

In another embodiment of the invention, an oligobenzothiophene-derivatized nucleoside is benzoterthiophene-2-deoxyriboside having the following structure:

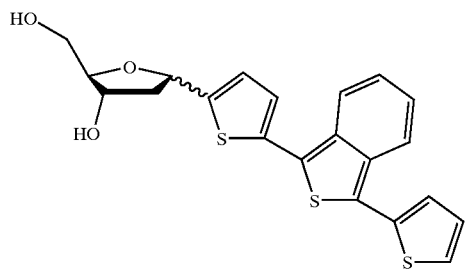

In another embodiment of the invention, an oligobenzothiophene-derivatized nucleoside is ter(benzothiophene)-2-deoxyriboside having the following structure:

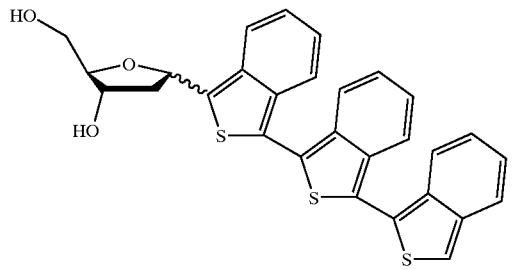

In another aspect of the invention, an oligo(phenylene vinylene)-derivatized nucleoside such as an oligo(phenylene vinylene)-derivatized deoxynucleoside has the general structure:

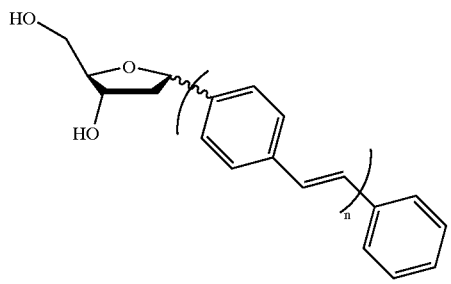

In another aspect of the invention, an oligo(phenylene vinylene)-derivatized nucleoside is styrylstilbene-2-deoxyriboside having the following structure:

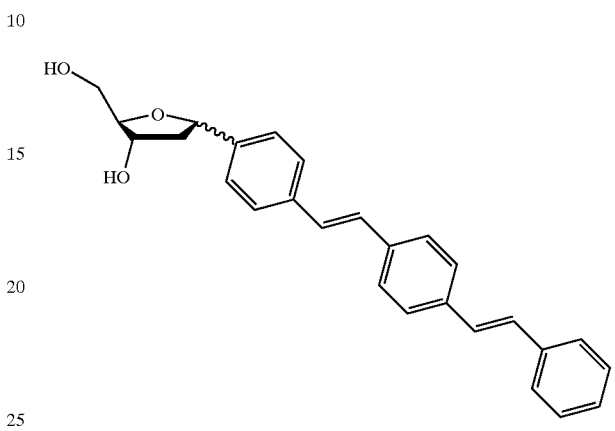

In yet another embodiment of the invention, a p-terphenyl-derivatized nucleoside such as a p-terphenyl-2-deoxyriboside has at least one of the following structures:

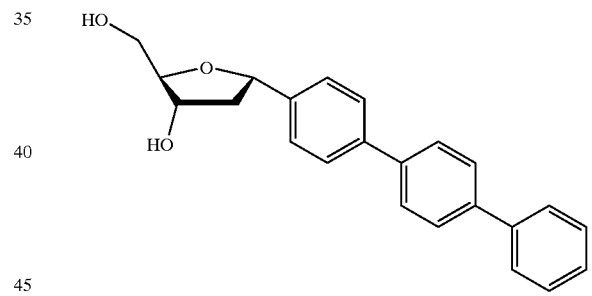

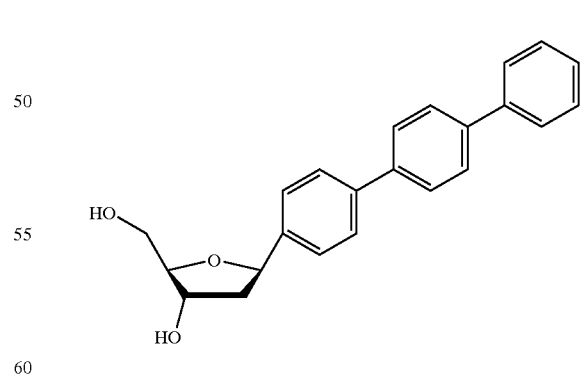

In another embodiment of the invention, a perylene-derivatized nucleoside such as a perylene-2-deoxyriboside has the following structure:

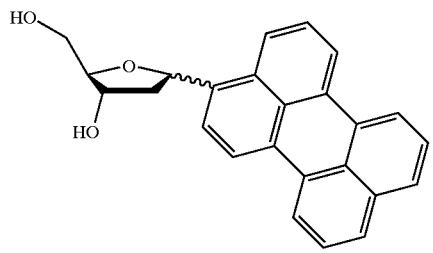

A perylene imide-derivatized nucleoside such as a perylene imide-2-deoxyriboside has the following structure:

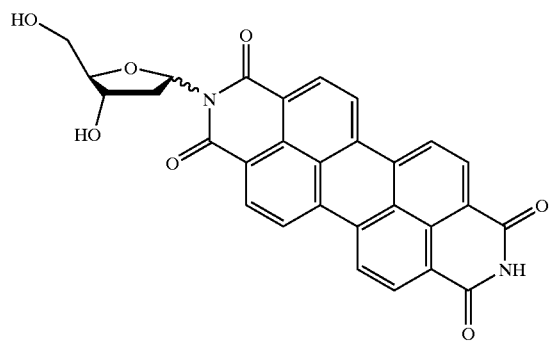

A perylene amide-derivatized nucleoside such as perylene amide-2-deoxyriboside has the following structure:

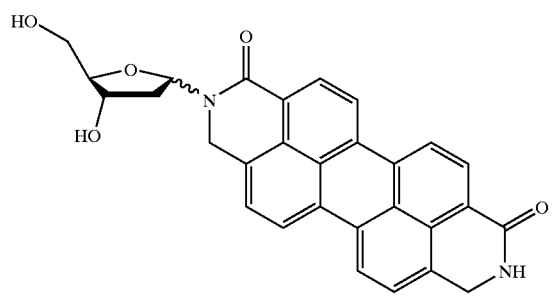

In another embodiment of the invention, a dimethylamino benzene-derivatized nucleoside such as dimethylamino benzene-derivatized deoxynucleoside has the following structure:

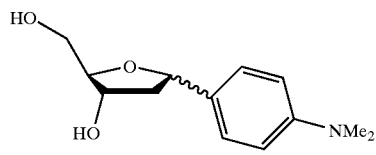

In accordance with the present invention, an oligo (phenylene acetylene) of varying length may be attached to a carbon atom of a sugar. Such a deoxyriboside analog may have the following chemical structure:

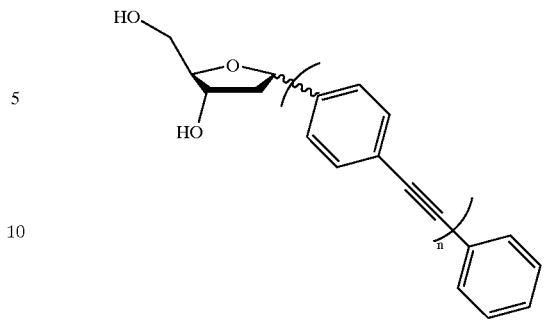

An example of such an oligo(phenylene acetylene) is e.g., diphenylacetylene-2-deoxyriboside having one of the following structures:

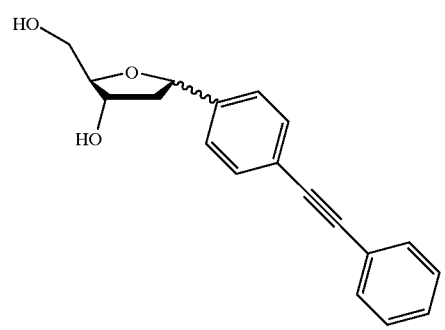

In yet another embodiment of the invention, an oligo (phenylene acetylene) of varying length such as e.g., phenyl (ethynyl)diphenylacetylene-2-deoxyriboside has one of the following structures:

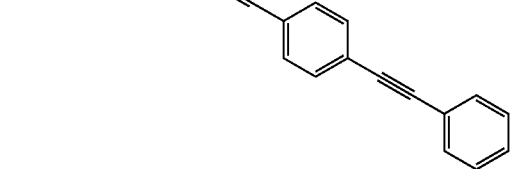

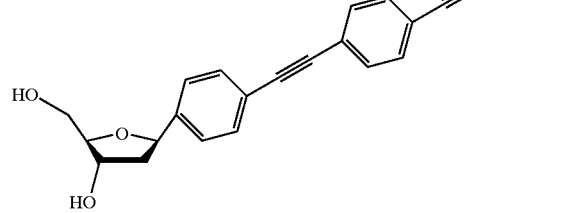

In accordance with the present invention, an azobenzene-derivatized nucleoside such as an azobenzene-2-deoxyriboside has the following structure:

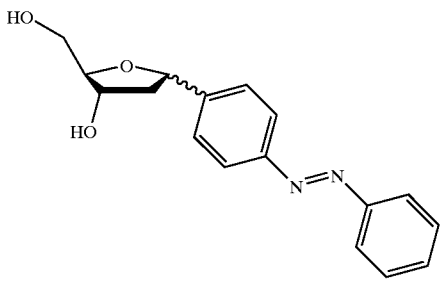

In another embodiment of the invention, a phenazine-derivatized nucleoside such as phenazine-2-deoxyriboside has one of the following structures:

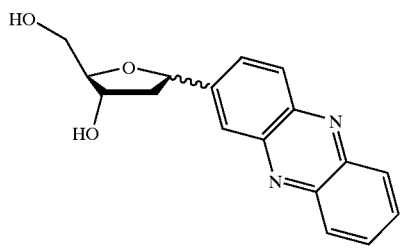

In still another embodiment of the invention, a napthalene-derivatized nucleoside such as napthalene-2-deoxyriboside has the following structure:

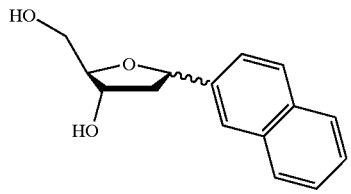

In yet another embodiment of the invention, a phenanthroline-derivatized nucleoside such as phenanthroline-2-deoxyriboside has the following structure:

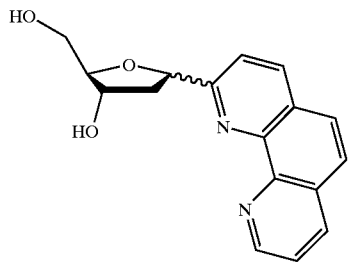

In still another embodiment, an acridine-derivatized nucleoside such as acridine-2-deoxyriboside has the following structure:

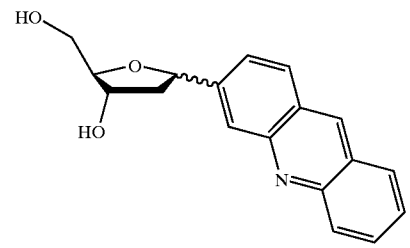

In another embodiment of the invention, a thioxanthrene-derivatized nucleoside such as thioxanthrene-2-deoxyriboside has the following structure:

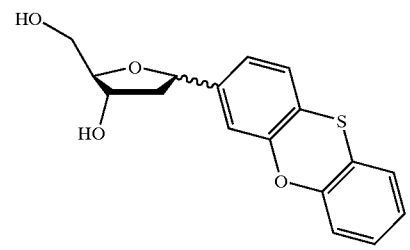

In still another embodiment of the invention, a chrysene-derivatized nucleoside such as chrysene-2-deoxyriboside has the following structure:

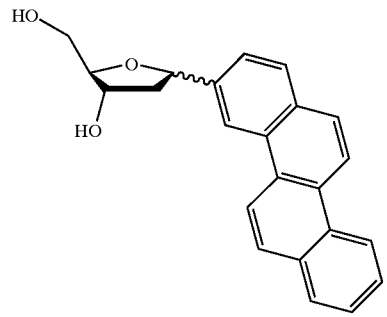

In still another embodiment of the invention, a rubrene-derivatized nucleoside such as rubrene-2-deoxyriboside has the following structure:

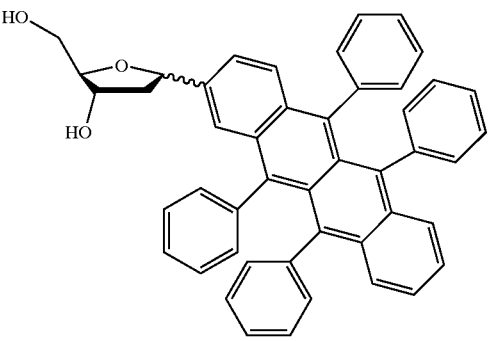

In still another embodiment of the invention, a coronene-derivatized nucleoside such as coronene-2-deoxyriboside has the following structure:

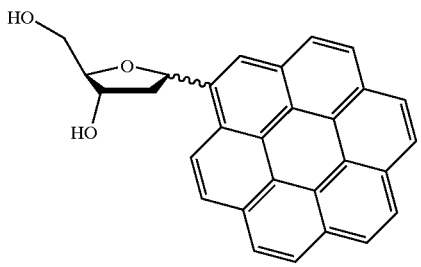

In yet another embodiment, a cyanine-derivatized nucleoside such as a cyanine-2-deoxyriboside has the following structure:

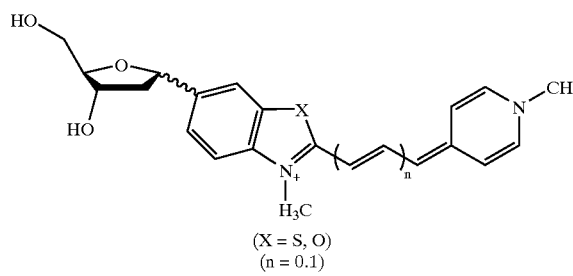

(X = S, O)
(n = 0.1)

In still another embodiment of the invention, a non-fluorescent nucleoside analog is provided such as cyclohexane-2-deoxyriboside having the following structure:

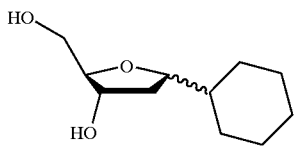

In another embodiment, a non-fluorescent nucleoside analog may be cyclohexene-2-deoxyriboside having the following structure:

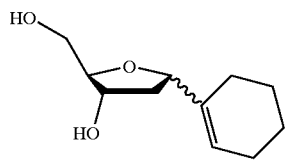

In still another embodiment, a non-fluorescent nucleoside analog may be decalin-2-deoxyriboside having the following structure:

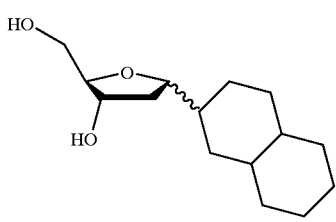

In yet another embodiment, a non-fluorescent nucleoside analog may be benzene-2-deoxyriboside having the following structure:

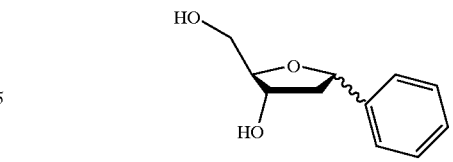

Useful intermediates provided by the present invention includes the fluorescent and non-fluorescent cyclic compound-derivatized nucleoside 5'-3'-paratoluoyl diesters. Examples are illustrated as 2a–2f of FIG. 2.

Other particularly useful intermediates provided by the present invention include, for example, the fluorescent and non fluorescent cyclic compound-derivatized 5'-dimethoxy trityl ethers. Examples are illustrated as 4a–4f in FIG. 2.

Useful phosphoramidite derivatives provided by the present invention include N,N-diisopropyl-O-cyanoethyl phosphoramidite derivitized at the 3' alcohol of the subject nucleoside analogs. Examples are illustrated as 5a–5f of FIG. 2.

The subject fluorescent cyclic compound-derivatized nucleosides, (also termed herein "subject nucleoside analogs", "subject fluorescent nucleosides" and "subject fluorophores") when incorporated into a nucleic acid such as RNA or DNA, provide fluorescence at a range of from about 350 nm to about 1100 nm emission maxima.

The subject fluorescent nucleosides of the present invention can be synthesized by coupling a fluorescent cyclic compound to a sugar using a modification of the organocadmium strategy described in Schweitzer and Kool (1995) *J. Am. Chem. Soc.* 117:1863. The non-fluorescent spacer molecules may be made the same methodology. The disclosure of this article and of all other articles cited in this application are incorporated herein as if fully set forth.

The C-nucleoside coupling involves the reaction of organocadmium or organozinc derivatives of the cyclic species with the well known a-chlorosugar synthon of Hoffer (Hoffer, M., (1960) *Chem Ber.* 93:2777). The glycosidic coupling of a cyclic compound to a sugar coupling results in a mixture of alpha and beta anomers in isolated yields of between about 54–81%. The primary product of this coupling reaction is the C1-coupled product formed with retention of configuration. Alpha-anomeric C-nucleotides are the primary reaction products. Although the alpha orientation is not the same as for natural β-nucleotides, alpha nucleosides are also known to form DNA-like helices (20) and models indicate that they can still interact well with natural bases in neighboring positions.

Toluoyl protecting groups may be removed in methanolic base. Thus, in accordance with the present invention, free unprotected nucleosides can be produced in as little as two steps: cyclic coupling and ester deprotection (FIG. 2). The alpha-anomers may be converted to the beta configuration by a third step, acid-catalyzed equilibration. A preferred acid catalyzed equilibration reaction uses benzenesulfonic acid in refluxing xylene, in the presence of a small amount of water.

The present invention also provides use of an oligomer of the subject nucleoside analogs which can be attached to generally any compound via a chemical bridge such as a thiol group. Methods for joining molecules can be found, for example, in S. L. Beaucage and R. P. Iyer (1993) *Tetrahedron* 49:1925–1963.

In addition, the present invention provides for oligonucleotide analogs in which fluorescent cyclic compounds replace some or all of the DNA or RNA bases. Natural oligonucleotides are strings of nucleosides bridged by phosphodiesters. Oligonucleotide analogs are oligonucleotides in which the structures of the bases, sugars, and/or phosphodiesters are modified to change or enhance molecular properties.

A chemical structure of a fully fluorophore-substituted subject oligonucleotide analog is provided below. In the structure depicted below, "fluorophore" is meant to encompass any of the subject nucleoside analogs described herein.

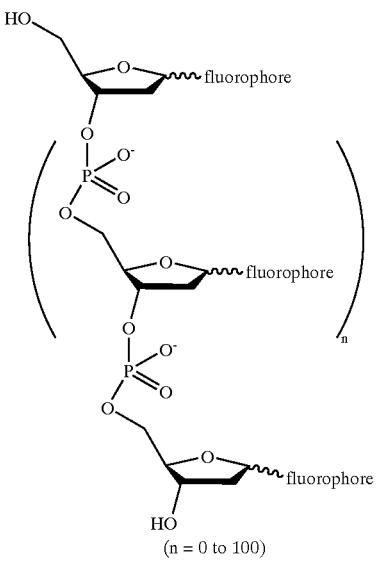

(n = 0 to 100)

The current invention provides oligonucleotide analogs where a base is replaced with a subject nucleoside analog, but also contemplates modifications in the sugar-phosphate backbones known to those familiar with the art. Examples of known oligonucleotide analogs in which the sugar or phosphate backbone is modified include phosphorothioate DNA, 2'-O-methyl RNA, phosphoramidate DNA, 2' fluoro DNA, peptide nucleic acid (PNA), and alpha-DNA. Thus, beyond using the natural DNA/RNA sugar-phosphate backbone, the present invention also contemplates oligonucleotide analogs having one or more of the bases replaced with fluorophores. The generalized structure for a PNA comprising the subject nucleoside analogs is shown below. In the structure depicted below, "fluorophore" is meant to encompass any of the nucleoside analogs of the present invention.

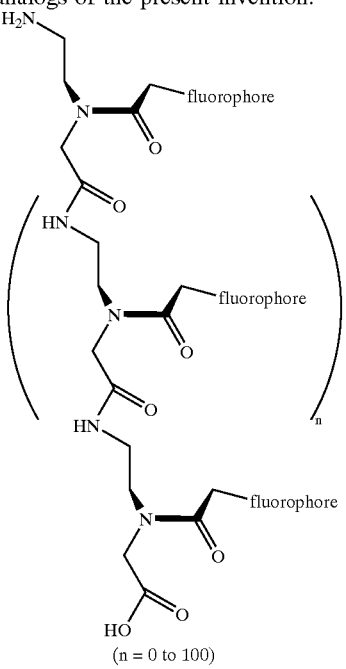

(n = 0 to 100)

The fluorescent cyclic compound-derivatized nucleosides of the present invention may be incorporated into an RNA or DNA strand during synthesis by any of a myriad of procedures known for making DNA or RNA. For example, such procedures include enzymatic synthesis and chemical synthesis. Chemical synthesis include solution or solid phase techniques.

Enzymatic methods of DNA oligonucleotide synthesis frequently employ Klenow, T7, T4, Taq or *E. coli* DNA polymerases as described in Sambrook et al. (1989, *Molecular Cloning: A Laboratory Manual*, Cold Spring Harbor Press, NY). Enzymatic methods of RNA oligonucleotide synthesis frequently employ SP6, T3, or T7 RNA polymerase as described in Sambrook et al. Reverse transcriptase can also be used to synthesize DNA from RNA (Sambrook et al.). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by PCR techniques as described, for example, by Saiki et al., 1988, *Science* 239:487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases in addition to the nucleoside base analogs of the present invention are incorporated into the oligonucleotide, and particularly if modified phosphodiester linkages are used, then the synthetic procedures are altered as needed according to known procedures. In this regard, Uhlmann et al. (1990, Chemical Reviews 90:543–584) provide references and outline procedures for making oligonucleotides with modified bases and modified phosphodiester linkages.

Synthetic oligonucleotides may be purified by polyacrylamide gel electrophoresis or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn, et al., 1982, *Nuc. Acid. Res.* 10:4671). Sequencing methods are also available for RNA oligonucleotides.

In a preferred method, DNA oligonucleotides are synthesized by automated methods using a DNA synthesizer and β-cyanoethylphosphoramidite chemistry. Extended coupling times (10 minute) are preferably used for the subject cyclic compound-derivatized nucleoside residues. Oligomers may be purified by preparative denaturing polyacrylamide gel electrophoresis and isolated by methods known in the art such as the crush and soak method.

The subject fluorescent nucleosides of the present invention can be incorporated into a nucleic acid in order to achieve fluorescence labeling. Standard methods may be used to convert the unprotected nucleosides to 5'-dimethoxytrityl-protected derivatives. For example, the unprotected subject nucleosides may be co-evaporated with dry pyridine, then dissolved in pyridine and methylenechloride. A catalytic amount of DMAP, and both diisopropylethylamine and 4,4'-dimethoxytrityl (DMT) chloride is then added and the mixture stirred at room temperature for about eight hours. Hexanes are added and the mixture loaded on a flash silica gel column and the product, 5'-dimethoxytrityl-protected derivatives, eluted. These derivatives may then be converted into cyanoethyl phosphoramidite derivatives for incorporation into a nucleic acid sequence such as DNA or RNA.

The preparation of 3'-O-phosphoramidites from the 5'-dimethoxytrityl-protected cyclic compound-derivatized nucleosides is achieved by methods well known in the art such as, for example, dissolving the protected nucleoside derivatives in dry methylene chloride and adding diisopropylethylamine and 2-cyanoethyl N,N,-diisopropylchlorophosphoramidite. The reaction mixture is stirred at room temperature for a period of about 4 hours after which hexanes are added. The mixture is then loaded to a flash silica gel column and the product eluted as an oil.

In accordance with the present invention, one or more of the subject nucleoside analogs may be incorporated at various positions in an RNA or DNA sequence. For example, one or more subject nucleoside analogs may be incorporated within a stretch of sequence so that the DNA or RNA fragment is effectively tagged towards the middle of the molecule. One or more subject nucleoside analogs may also be incorporated near or at the end of an RNA or DNA sequence.

In another aspect of the invention, one or more of the subject nucleoside analogs may be incorporated within a linear nucleic acid molecule, or at either or both the 5' or 3' ends of a linear nucleic acid molecule. The subject fluorescent nucleosides may be present in more than one position in an RNA or DNA molecule. In a preferred embodiment, at least two subject nucleosides are placed adjacent to one another within an RNA or DNA sequence. The RNA or DNA sequence may comprise a linear, hairpin, dumbbell, circular, or branched conformation and may be single or double stranded.

The DNA and RNA sequences comprising one or more anucleoside analogs of the present invention are useful for detecting target nucleic acids in tissues, genomic material such as chromatin and chromosomes, solutions or immobilized on membranes. Desirable properties of fluorophores include intense fluorescence (which depends on absorbance and quantum yield) and choices of multiple wavelengths of emission. The subject nucleoside analogs offer extremely high absorbance and many possible wavelengths. Another desirable property of fluorophores is a long Stokes shift as it helps avoid background fluorescence. The nucleoside analogs of the present invention have among the longest Stokes shifts known.

The fluorescently labeled nucleoside derivatives of the present invention are particularly useful when attached to a solid support such as controlled pore glass (cpg). Thus, the DNA and RNA sequences comprising a nucleoside analog of the present invention hybridize to a target nucleic acid of sufficient complementarity in the detection of such targets by contacting the derivitized probe with the target in a sample to be tested for a time and under conditions sufficient to detectably hybridize the probe with the target. The present nucleoside derivatives are particularly useful in any technique which uses fluorescent-tagged oligonucleotides for detection. A rapidly growing diagnostic technique which involves fluorescence detection is fluorescence in situ hybridization (FISH). The method uses long, enzymatically synthesized DNA strands tagged with multiple fluorescent labels. These are hybridized to fixed chromosomes from a patient's cell, and if the gene in question is present, a colored fluorescent spot is visible on the chromosome by fluorescence microscopy. The method is used to detect whole genes such as the bcr/abl translocated gene in CML, or extra copies of genes in certain genetic diseases.

Small synthetic oligonucleotides are expected to have much higher sequence specificity than long traditional FISH probes. For FISH to work, a probe must be fluorescent-labeled brightly enough to detect under the microscope. Thus, an oligonucleotide must carry the equivalent of several (roughly~8–40) fluorescent tags. The fluorescent nucleoside analogs of the present invention give greater brightness when used as multiple labels. Thus, multiple nucleoside analogs incorporated next to each other in a nucleic acid molecule give strong excimer fluorescence. The intensity of the peak generally increases with the number of fluorophores and the excimer to monomer emission ratio increases as well.

Specific applications of the subject fluorescent nucleosides in labeling nucleic acids include: fluorescent primers for automated DNA sequencing, fluorescent probes for flow cytometry, fluorescent probes for ELISA-like sandwich assays, fluorophores for measurement of protein-DNA binding, fluorescent primers for detection/identification after or during PCR, fluorescent probes for in situ hybridization/microscopy (RNA and DNA targets),measurement of cellular uptake of DNA, measurement of distance, orientation and dynamics in nucleic acid structures, and fluorescent probes for Southern/Northern blots and related assays.

In another aspect of the invention, there are provided compositions and methodologies for constructing combinatorial arrays of fluorophores (CFAs) built on a nucleic acid backbone. The combinatorial arrays are built from a library of the subject nucleoside analogs, hereinbefore described in detail. Other fluorescent nucleoside analogs such as anthracene, phenanthrene, tetracene and pentacene-derivatized nucleosides described in copending U.S. patent application Ser. No. 08/857,721, may also be used in the CFAs of the present invention.

In one embodiment, a library is constructed on multiple solid supports such as Tentagel® beads using well known split-and-pool methods such as those described in Ohlmeyer M H et al. (1993) "Complex synthetic chemical libraries indexed with molecular tags." Proc Natl Acad Sci USA (90):10922–10926.

Other supports which can be used to attach the nucleoside analogs include e.g., polystyrene, PMMA, polyacrylamide, cellulose, controlled pore glass, or geysen pins. Alternatively, arrays may be separated in space on one or more large solid supports. Examples of larger size supports include e.g., glass, microscope slides, micro titer dishes, and tea bags. In this embodiment, a final library of fluorophore arrays is produced in which each solid support from a collection of multiple solid supports, or each location on a large solid support, has attached thereto, only one type of oligomeric sequence comprising the subject fluorescent nucleoside analogs. The library is made up of many of such solid supports or locations on one or more large solid supports. Thus, members of the library may be different with respect to one another due to their individual nucleoside analog makeup. In this embodiment, only the subject nucleoside analogs are incorporated into an oligomer. FIG. 5 illustrates this embodiment of the invention. An oligomer in this sense, is meant to include as little as about two subject nucleoside analogs and as many as about one hundred.

In another embodiment, unlabeled, non-fluorescent nucleosides or nucleic acid sequences are added to the solid supports, either 5' or 3' to the subject nucleoside analogs or interspaced between the nucleoside analogs. In still another embodiment of the invention, one or more subject non-fluorescent nucleoside analogs (i.e., spacer molecules) such as e.g., cyclohexane-2-deoxyriboside, cyclohexene-2-deoxyriboside, decalin-2-deoxyriboside, or benzene-2-deoxyriboside, are interspaced between the fluorescent nucleoside analogs or between fluorescent nucleoside analogs and non-labeled nucleosides. The incorporation of one or more subject non-fluorescent nucleoside analogs, which act as spacer molecules, prevents quenching of fluorescence by the natural nucleoside bases.

Members of the library may be selected based on absorption and emission characteristics. Selection of beads with interesting and useful fluorescence characteristics is performed by fluorescence microscopy or the naked eye under ultraviolet light, transilluminator, or other forms of fluorescence imaging.

To aid in the identification of one or more desired members of a subject CFA library, the libraries may be encoded using the methods described in Ohlmeyer M. H., et al., (1993) "Complex synthetic chemical libraries indexed with molecular tags." *Proc. Natl. Acad. Sci USA* 90:10922–10926. Identification of a sequence on a given bead is carried out by chemical treatment of the bead, followed by gas chromatography. If desired, the sequence may be made again on a preparative scale in order to better characterize it. Many other combinatorial deconvolution methods are known to those of skill in the art and may be used to help identify one or more members of the library.

The present invention also provides a method for selecting a fluorophore suitable for use in labeling a nucleic acid. The method comprises constructing a combinatorial fluorophore array library as described above and selecting a particular nucleoside analog or sequence of nucleoside analogs which emits the most intense fluorescence, or which emits a specific wavelength of light. Selection may be performed using fluorescence microscopy, naked eye under UV light, or transilluminator.

In yet another embodiment of the invention, there is provided a method for identifying a subject nucleoside analog which exhibits significant Stokes shifts. The method entails exciting a subject CFA library at a short wavelength and selecting one or more fluorophore arrays which emit at much longer wavelengths. The range of short wavelength useful for practicing this aspect of the invention is about 200 nm to about 1000 nm. Selection is done as described above.

In still another embodiment of the invention, there is provided a method of identifying a fluorophore involved in energy transfer to or from another dye on a different nucleic acid molecule. The method comprises constructing a subject CFA library and hybridizing a nucleic acid comprising a donor or acceptor dye to a nucleic acid sequence in the CFA library. A change in color in the hybridized molecule indicates that energy transfer has taken place.

In still another embodiment of the invention, a method for identifying a fluorophore sequence that changes its emission wavelength or intensity on binding an analyte is provided. The method comprises constructing a combinatorial fluorophore array library, incorporating an analyte affinity molecule into the oligomers attached to the solid support(s), allowing an analyte solution to contact the library, and selecting library members that change emission wavelength intensity or wavelength on binding of the analyte molecule.

The following examples further illustrate the invention.

EXAMPLE 1

General Synthesis Methods

The previously described method (18, 19) of C-nucleoside coupling was utilized to generate the nucleoside analogs 3a–3f (FIG. 1). The method involves cadmium- or zinc-mediated reaction of Grignard derivatives of cyclic compounds with Hoffer's chlorosugar (FIG. 2) [18,19]. The primary product in this coupling reaction is the C1α-coupled product, formed with retention of configuration.

Solvents used as reaction media were purified and dried by distillation over $CaH_2$ (pyridine, MeCN and $CH_2Cl_2$), Na (THF) or MeONa (MeOH) before use. Chemicals were purchased from Acros, Aldrich, Alfa-Aesar, Lancaster, Fisher, or J. T. Baker. Flash chromatography (FC): silica gel MéMerck 60, 0.040–0.063 mm. $^1$H-NMR (400 MHz) and $^{13}$C-NMR (100 MHz) in $CDCl_3$ unless otherwise stated; Bruker-Avance 400 spectrometer; chemical shifts in ppm rel. to TMS, coupling constants J in Hz. High resolution mass spectral analyses (HRMS) were performed by the University of California-Riverside Mass Spectrometry Facility. EI-MS: HP 5973 Mass selective detector. Abbreviations: DIEA=N,N-diisopropylethylamine, DMAP=4-dimethylaminopyridine, DMT=4,4'-dimethoxytrityl, EtOAc=ethyl acetate, MeCN=acetonitrile, $PdCl_2(dppf)_2$=[1,1'-bis(diphenylphosphino)ferrocene]dichloropalladium(II), TEA=triethylamine.

1-bromopyrene was purchased and used to prepare benzoterthiophene [22], 4-bromo-p-terphenyl [23], 4-bromostilbene [24] and 1-bromocyclohexene [25] using the literature procedures. Bromoterthiophene was prepared as illustrated in FIG. 3. Subsequent coupling reactions with the chlorosugar [26] were performed as described previously giving yields of 23–55% for the coupled products. The pyrene nucleoside (3d of FIG. 1) was also prepared by this approach, as previously described [10]. The toluoyl protecting groups on all the nucleosides were then removed, generating the free nucleosides (3a–f, FIG. 1). These were examined for their fluorescence characteristics. For future studies in which these fluorophores are incorporated into nucleic acid molecules the terthiophene, benzoterthiophene, p-terphenyl, pyrene, stilbene and cyclohexane (3a–f, FIG. 1) were used to prepare the 5'-dimethoxytrityl protected nucleosides (compounds 4a–f, FIG. 2) and then the 3'-O-phosphoramidites (compounds 5a–f, FIG. 2).

The syntheses proceeded as expected except for the benzoterthiophene case. During the synthesis of the benzoterthiophene-derivatized nucleoside significant decomposition was observed. To see if it was thermal or photodecomposition, two NMR-samples of the bistoluoyl nucleoside (2b, FIG. 2) were prepared in deuterochloroform. One sample was kept exposed to fluorescent room light and the other sample was kept wrapped in aluminum foil.

$^1$H-NMR-spectra were measured immediately after preparation, after 1 day and after 7 days. It was found that the spectrum of the sample wrapped into aluminum foil remained unchanged whereas decomposition of the nucleoside (2b, FIG. 2) could be observed in the sample which was exposed to light for 7 days. Subsequently, all experiments with the benzoterthiophene derivatives were carried out with limited light exposure by covering glassware with aluminum foil. In this last case, the best success in coupling with the chlorosugar was seen with the debrominated form of 1b, FIG. 2; in that case, direct deprotonation formed the organolithium species which was then exchanged with $CdCl_2$ to give the analogous organocadmium-mediated reaction.

General Procedure A

A solution of the arylbromide in dry THF was slowly added to Mg-turnings in dry THF. To start the Grignard reaction, a few drops of 1,2-dibromoethane were added and the mixture was slightly heated. After complete addition of the arylbromide solution, the reaction mixture was stirred for 2 h at 50° C. $CdCl_2$ was then added and the mixture was stirred for 2 h at reflux. The reaction was cooled to room temperature and a solution of the Hoffer's chlorosugar in THF was added. After stirring for 16 hours at room temperature, the solvent was evaporated, the residue was suspended in $CH_2Cl_2$ and washed twice with 10% $NH_4Cl$ soln. The aqueous layers were extracted with $CH_2Cl_2$ and the organic layers were dried ($MgSO_4$) and concentrated. Purification by FC (hexanes/EtOAc 6:1) gave the pure α-anomers (the β-anomers as minor products were not isolated).

General Procedure B

Freshly prepared 0.5 M $NaOCH_3$ in MeOH was added to a solution of the protected nucleoside in MeOH/$CH_2Cl_2$ 1:1. After stirring for 4 hours at room temperature, crystalline $NH_4Cl$ was added and the solvent was evaporated. Purification by FC (EtOAc) gave the pure deprotected nucleosides.

General Procedure C

The deprotected nucleoside was coevaporated twice with pyridine and then dissolved in pyridine/$CH_2Cl_2$. DMT-Cl, DIEA and a catalytic amount of DMAP were added and the reaction mixture was stirred for 4–8 hours at room temperature. The solvents were then evaporated and the residue was purified by FC (hexanes/EtOAc 4:1→1.5:1, preequilibrated with hexanes containing 5% TEA).

General Procedure D

2-Cyanoethyl N,N-diisopropylchlorophosphoramidite and DIEA were added to a solution of the DMT-protected nucleoside in $CH_2Cl_2$ and the mixture was stirred for 5 hours at room temperature. The solvent was evaporated and the residue was purified by FC (hexanes/EtOAc 3:1, preequilibrated with hexanes/EtOAc 3:1 containing 5% TEA)

EXAMPLE 2

Synthesis of the Terthiophene Nucleoside 5-bromo-2,2'-bithiophene (6, FIG. 3)

A solution of 2-bromothiophene (4.967 g, 24.92 mmol) in 5 ml dry THF was added dropwise to a mixture of Mg-turnings (752 mg, 30.94 mmol) and a small iodine crystal in 25 ml dry THF. After addition of about 1 ml of the bromothiophene solution, the reaction started and the mixture heated to reflux. The rest of the bromothiophene solution was added dropwise to the reaction, and the mixture was stirred for 1 hour at reflux. The reaction mixture was then transferred with a syringe into an addition funnel and was added slowly during 3 hours to an ice-cooled mixture of 2,5-dibromothiophene (8.206 g, 33.91 mmol) and $PdCl_2$(dppf)$_2$ (250 mg, 0.306 mmol, complex with $CH_2Cl_2$ 1:1) in 50 ml dry THF. This mixture was stirred for 2 hours at 0° C. and for 16 hours at room temperature. The solvent was evaporated in vacuo and the residue was suspended in EtOAc and washed with saturated $NaHCO_3$ solution and brine. The aqueous layers were extracted with EtOAc and the organic layers were dried ($MgSO_4$). Evaporation of the solvent and purification by FC (hexanes) gave 4.229 g 5-bromo-2,2'-bithiophene (6, FIG. 3) (17.25 mmol, 57%) and 1.216 g 2,2':5',2"-terthiophene (7, FIG. 3) (4.896 mmol, 16%) as yellow solids. 6:$^1$H-NMR: 7.22 (dd, J=5.2, 0.8, 1 H), 7.11 (dd, J=3.6, 0.8, 1 H), 7.00 (dd, J=5.2, 3.6, 1 H), 6.96 (d, J=3.9, 1 H), 6.91 (d, J=3.9, 1 H). $^{13}$C-NMR: 138.9, 136.4 (2s), 130.6, 127.8, 124.8 (3d), 124.3 (s), 124.0, 123.8 (2d). EI-MS: 246 (100, [M]$^+$, $^{81}$Br), 244 (88, [M]$^+$, $^{79}$Br), 165 (39), 121 (53).

5-bromo-2,2':5',2"-terthio-hene (1a, FIG. 3)

Using 5-bromo-2,2'-bithiophene (6, FIG. 3): A solution of 5-bromo-2,2'-bithiophene (3.052 g, 12.45 mmol) in 20 ml dry THF was added dropwise to a mixture of Mg-turnings (332 mg, 13.66 mmol) and a small iodine crystal in 10 ml dry THF. To start the Grignard reaction, the reaction mixture was heated to reflux. After addition of the bromobithiophene solution, the reaction mixture was stirred for 2 hours at reflux. It was then cooled to room temperature, transferred with a syringe into an addition funnel and added dropwise during 2 hours to a mixture of 2,5-dibromothiophene (3.031 g, 12.53 mmol) and $PdCl_2$(dppf)$_2$ (113 mg, 0.138 mmol, complex with $CH_2Cl_2$1:1) in 50 ml dry THF at −20° C. This mixture was stirred for 2 hours at −20° C. and then for 14 hours at room temperature. The solvent was evaporated in vacuo and the residue was dissolved in $CH_2Cl_2$ and washed with 5% HCl and brine. The aqueous layers were extracted with $CH_2Cl_2$ and the organic layers were dried ($MgSO_4$). Evaporation of the solvent and purification by FC (hexane) gave 1.597 g (39%) 5-bromo-2,2':5',2"-terthiophene (1a, FIG. 3).

Using 2,2':5',2"-terthiophene (7, FIG. 3): N-Bromosuccimide (3.147 mg, 17.681 mmol) were added portion in portions during 5 hours to an solution of 2,2':5', 2"-terthiophene (4.315 g, 17.373 mmol) in 10 ml DMF at −20° C. After about 90 min, a precipitate was formed. After stirring for 14 hours at room temperature, the reaction mixture was dissolved in 300 ml $CH_2Cl_2$ and washed twice with 100 ml 1N HCl. The aqueous layers were extracted with $CH_2Cl_2$ and the organic layers were dried ($MgSO_4$) and concentrated. Purification by FC (hexanes) gave 5.222 g (56 mmol, 92%) 5-bromo-2,2':5',2"-terthiophene, 92%) as yellow solid.

$^1$H-NMR: 7.23 (dd, J=5.2, 1.0, 1 H), 7.17 (dd, J=3.6, 1.0, 1 H), 7.07 (d, J=3.7, 1 H), 7.02 (dd, J=5.3, 3.6, 1 H), 7.01 (d, J=3.6, 1 H), 6.98 (d, 3.9, 1 H), 6.91 (d, J=3.8, 1 H). $^{13}$C-NMR (CDCl$_3$): 138.6, 136.8, 136.7, 135.0, 130.7, 127.9, 124.7, 124.5, 124.3, 123.9, 123.7, 111.0. EI-MS: 328 (100, [M]$^+$, $^{81}$Br), 326 (88, [M]$^+$, $^{79}$Br), 247 (15), 203 (32).

1',2'-Dideoxy-1'α-[2,2':5',2"]terthiophen-5-yl-3',5'-di-O-toluoyl-D-ribofuranose (2a, FIG. 2)

According to Procedure A. Reaction of 5-bromo-2,2':5', 2"-terthiophene (1a, FIG. 3) (1.809 g, 5.528 mmol) in 15 ml THF with Mg-turnings (141 mg, 5.802 mmol) in 2 ml THF, $CdCl_2$ (1.021 g, 5.569 mmol) and Hoffer's chlorosugar (2.144 g, 5.514 mmol) in 10 ml THF gave 1.816 g (3.022 mmol, 55%) 1',2'-Dideoxy-1'α-[2,2':5',2"]terthiophen-5-yl-3',5'-di-O-toluoyl-D-ribofuranose (2a, FIG. 2) as yellow foam.

¹H-NMR: 7.97, 7.83 (2d, J=8.2, 4 arom. H), 7.24–7.16 (m, 6 arom. H), 7.07 (d, J=3.8, 1 arom. H), 7.03–7.01 (m, 3 arom. H), 6.91 (d, J=3.5, 1 arom. H), 5.62 (m, H-C(3')), 5.57 (dd, J=7.5, 4.9, H-C(1')), 4.70 (m, H-C(4')), 4.58 (m, 2 H-C(5'), 2.96, 2.47 (2m, 2 H-C(2')), 2.41, 2.39 (2s, 2 MePh). ¹³C-NMR: 166.3, 166.1 (2 C=O), 145.5, 144.0, 143.9, 137.1, 136.7, 136.1 (6s, 7 arom. C), 129.73, 129.71, 129.1, 129.0, 127.9 (5d, 9 arom. CH), 127.0, 126.8 (2s, 2 arom. C), 125.0, 124.5, 124.3, 124.1, 123.6, 123.2 (6d, 6 arom. CH), 82.1, 76.8, 76.2 (3d, H-C(1'), H-C(3'), H-C(4')), 64.4, 40.3 (2t, H$_2$-C(5'), H$_2$-C(2')), 21.7 (q, H$_3$CPh). HRMS calcd. for C$_{33}$H$_{28}$O$_5$S$_3$ ([M]$^+$): 600.1099, found: 600.1109.

1',2'-Dideoxy-1'α-[2,2':5',2"]terthiophen-5-yl-D-ribofuranose (3a, FIG. 2)

According to Procedure B. Treatment of 2a (535 mg, 0.891 mmol) with 0.5M NaOMe in MeOH (1 ml, 0.5 mmol) in 5 ml MeOH/CH$_2$Cl$_2$ 1:1 gave 235 mg (3a, FIG. 2) (0.645 mmol, 72%) as yellow crystals.

¹H-NMR: 7.25–6.93 (m, 7 arom. H), 5.35 (m, H-C(1')), 4.49, 4.10 (2m, H-C(3'), H-C(4')), 3.86, 3.76 (2m, 2 H-C(5'), 2.75, 2.26 (2m, 2 H-C(2')). ¹³C-NMR (d$_5$-pyridine): 148.2, 137.4, 136.9, 136.3 (4S), 128.6, 125.4, 125.1, 124.7, 124.4, 123.9 (6d, 7 arom. CH), 87.7, 76.1, 72.8 (3d, H-C(1'), H-C(31), H-C(4')), 63.0, 44.8 (2t, H$_2$-Cl (5'), H$_2$-C(2')). HRMS calcd. for C$_{17}$H$_{16}$O$_3$S$_3$ ([M]$^+$): 364.0262, found: 364.0273.

1',2'-Dideoxy-5'-O-(4,4'-dimethoxytrityl)-1'α-[2,2':5',2"]terthiophen-5-yl-D-ribofuranose (4a, FIG. 2)

According to Procedure C. DMT-Cl (269 mg, 0.794 mmol), DIEA (115 µl, 0.672 mmol) and a spatula tip of DMAP were added to a solution of 3a (161 mg, 0.442 mmol) in 8 ml pyridine/CH$_2$Cl$_2$ 1:1 and stirred for 6 h. Purification gave 268 mg 4a, FIG. 2 (0.402 mmol, 91%) as yellowish foam.

¹H-NMR: 7.50 (d, J=7.5, 2 arom. H), 7.41–7.19, 7.10–7.04 (2m, 13 arom. H), 6.95 (d, J=3.5, 1 arom. H), 6.88 (d, J=8.8, 4 arom. H), 5.36 (t, J=7.0, H-C(1')), 4.45 (m, H-C(3')), 4.21 (m, H-C(4')), 3.82 (s, 2 OCH$_3$), 3.38, 3.27 (2m, 2 H-C(5')), 2.75, 2.21 (2m, 2 H-C(2')). ¹³C-NMR: 158.5, 145.9, 144.7, 137.1, 136.7, 136.2, 136.1, 135.9 (8s, 10 arom. C), 130.0, 128.1, 127.9, 126.9, 125.0, 124.5, 124.3, 124.2, 123.7, 123.3, 113.2 (11d, 20 arom. CH), 86.4 (s, 1 C), 84.4, 75.9, 74.8 (3d, H-C(1'), H-C(3'), H-C(4')), 64.5 (t, H$_2$-C(5')), 55.2 (q, 2 OCH$_3$), 42.9 (t, H$_2$-C(2')). HRMS calcd. for C$_{38}$H$_{34}$NaO$_5$S$_3$ ([M+Na]$^+$): 689.1466, found: 689.1430.

1',2'-Dideoxy-5'-O-(4,4'-dimethoxytrityl)-1'α-[2,2':5',2"]terthiophen-5-yl-D-ribofuranose cyanoethyl N,N-diisopropylphosphoramidite (5a, FIG. 2)

According to Procedure D. 2-Cyanoethyl diisopropylchlorophosphoramidite (172 mg, 0.726 mmol) and DIEA (350 µl, 2.044 mmol) were reacted with 4a, FIG. 2 (313 mg, 0.469 mmol) in 5 ml CH$_2$Cl$_2$. Purification gave 321 mg 5a, FIG. 2 (0.370 mmol, 79%) as yellowish foam.

¹H-NMR (mixture of 2 diastereoisomeres): 7.53–7.50, 7.42–7.17, 7.09–7.01, 6.93–6.91, 6.86–6.82 (5m, 20 arom. H), 5.43 (m, H-C(1')), 4.57, 4.34 (2m, H-C(3'), H-C(4')), 3.81, 3.80 (2s, 2 OCH$_3$), 3.72–3.48, 3.38–3.27, 3.17–3.13 (3m, 2 NCH(CH$_3$)$_2$, OCH$_2$CN, 2 H-C(5')), 2.75 (m, 1 H-C(2')), 2.56–2.51 (m, OCH$_2$CH$_2$CN), 2.37 (m, 1 H-C(2')), 1.17–1.03 (m, 2 NCH(CH$_3$)$_2$). ¹³C-NMR: 158.4, 146.1, 144.9, 137.1, 136.4, 136.1, 136.0 (7s, 10 arom. C), 130.1, 128.2, 127.9, 127.8, 126.7, 124.9, 124.4, 124.3, 124.0, 123.6, 123.2 (11d, 16 arom. CH), 117.5 (s, CN), 113.1 (d, 4 arom. CH), 86.1 (s, 1 C), 84.7, 76.3 (2d, H-C(1'), H-C(4')) 75.0, 74.8 (2d, H-C(3')), 63.8 (t, H$_2$-C(5')), 58.2, 58.1 (2t, OCH$_2$CH$_2$CN), 55.2 (q, 2 OCH$_3$), 43.2, 43.1 (2d, 2 NCH (CH$_3$)$_2$), 42.4 (t, H$_2$-C(2')), 24.6, 24.5, 24.4, 24.3 (4q, 2 NCH(CH$_3$)$_2$), 20.1, 20.0 (2t, OCH$_2$CH$_2$CN). HRMS calcd. for C$_{47}$H$_{51}$N$_2$NaO$_6$PS$_3$ ([M+Na]$^+$): 889.2545, found: 889.2532.

EXAMPLE 3

Synthesis of Benzoterthiophene Nucleoside

For the synthesis of the benzoterthiophene nucleosides, all flasks and columns were wrapped in aluminum foil to prevent photodecomposition.

1',2'-Dideoxy-1'α-[5-(3-thiophen-2-yl-benzo[c]thiophen-1-yl)-thiophen-2-yl]-3',5'-di-O-toluoyl-D-ribofuranose (2b, FIG. 2)

The reaction was performed under absence of light (flasks wrapped in alumina foil). n-BuLi (2.5M in hexane, 1 ml, 2.5 mmol) was slowly added to a solution of 1,3-dithiophen-2-yl-benzo[c]thiophene [22] in 40 ml THF at −68° C. and stirred for 90 min. CdCl$_2$ (281 mg, 1.533 mmol) was added at −68° C., the reaction mixture was allowed to warm up to room temperature and was stirred for 2 hours at room temperature. A solution of Hoffer's chlorosugar (831 mg, 2.137 mmol) in 20 ml THF was added and stirred for 16 hours. Then the solvent was evaporated, the residue was dissolved in CH$_2$Cl$_2$ and washed twice with 10% NH$_4$Cl solution. The aqueous layers were extracted with CH$_2$Cl$_2$ and the organic layers were dried (MgSO$_4$) and concentrated. Purification by FC (hexane/EtOAc 7:1) gave 678 mg 2b, FIG. 2 (1.041 mmol, 49%) and 231 mg recovered unreacted benzoterthiophene (0.774 mmol, 37%).

¹H-NMR: 8.01–7.85 (m, 6 arom. H), 7.41–7.06 (11m, 13 arom. H), 5.68–5.64 (m, H-C(1'), H-(3')), 4.77, 4.62 (2m, H-C(4'), 2 H-C(5')), 3.02 (m, H-C(2')), 2.45 (s, MePh), 2.57 (m, H-C(2')) 2.44 (s, MePh), 2.38 (s, MePh). ¹³C-NMR: 166.4, 166.1 (2 C=O), 143.9, 143.8, 141.6, 140.6, 140.1, 139.7 (6s, arom. C), 129.7, 129.6, 129.1, 129.0, 128.8, 127.5, 127.4, 127.1, 127.0 (10d, 19 arom. CH) , 126.8 (s, arom. C), 126.1 (d, 2 arom. CH), 82.2, 80.0, 76.4 (3d, H-C(1'), H-C(3'), H-C(4')),64.6, 40.3 (2t, H$_2$-C(5'), H$_2$-C (2')), 21.67, 21.63 (2q, 2 H$_3$CPh). HRMS calcd. for C$_{37}$H$_{31}$O$_5$S$_3$ ([M+H]$^+$): 651.1334, found: 651.1358.

1',2'-Dideoxy-1'α-[5-(3-thiophen-2-yl-benzo[c]thiophen-1-yl)-thiophen-2-yl]-D-ribofuranose (3b, FIG. 2)

According to Procedure B. Reaction was performed under absence of light (flasks wrapped in alumina foil). Treatment of 2b, FIG. 2 (548 mg, 0.842 mmol) with 0.5M NaOMe in MeOH (850 µl, 0.425 mmol) in 5 ml MeOH/CH$_2$Cl$_2$ 1:1 gave 243 mg 3b, FIG. 2 (0.586 mmol, 70%) as a dark yellow solid.

¹H-NMR (THF-d$_8$): 7.97–7.91 (m, 2 arom. H), 7.48 (d, J=4.9, 1 arom. H), 7.38 (d, J=3.2, 1 arom. H), 7.24–7.21, 7.15–7.10, 7.02–7.00 (3m, 5 arom. H), 5.28 (t, J=7.4, H-C(1')), 4.41, 4.29, 3.90 (3m, H-(3'), H-C(4'), 2 OH), 3.67–3.55 (m, 2 H-C(5')), 2.66, 2.08 (m, 2 H-C(2')). ¹³C-NMR (THF-d$_8$): 146.8, 133.4, 133.3, 133.1, 132.3, (5s, 5 arom. C), 125.9 (d, 1 arom. CH), 124.9, 124.0 (2s, 2 arom. C), 123.7, 123.5, 123.0, 122.8, 122.7, 122.4, 119.5, 119.3 (8d, 8 arom. CH), 84.5, 73.7, 70.1 (3d, H-C(1'), H-C(3'), H-C(4')), 60.3, 42.1 (2t, H$_2$-C(5'), H$_2$-C(2')).

1',2'-Dideoxy-5'-O-(4,4'-dimethoxytrityl)-1'α-[5-(3-thiophen-2-yl-benzo[c]thiophen-1-yl)-thiophen-2-yl]-D-ribofuranose (4b, FIG. 2)

According to Procedure C. Reaction was performed under absence of light (flasks wrapped in aluminum foil). DMT-Cl (210 mg, 0.620 mmol), DIEA (180 µl, 1.051 mmol) and a spatula tip of DMAP were added to a solution of 3b, FIG. 2 (104 mg, 0.251 mmol) in 5 ml pyridine/$CH_2Cl_2$ 1:1 and stirred for 3 days. Purification gave 94 mg 4b, FIG. 2 (0.131 mmol, 52%) as dark yellow foam.

$^1$H-NMR: 7.99–7.95 (m, 2 arom. H), 7.49–7.15 (m, 15 arom. H), 7.06 (d, J=3.6, 1 arom. H), 6.87 (d, J=8.8, 4 arom. H), 5.42 (t, J=7.1, H-C(1')), 4.47, 4.21 (2m, H-C(3'), H-C(4')), 3.82 (s, 2 $OCH_3$), 3.46 (dd, J=9.5, 4.4, H-C(5') ), 4.21 (dd, J=9.5, 6.0, H-C(5')), 2.81 (m, 1 H-C(2')), 2.31–2.24 (m, 1 H-C(2'), 1 OH), 2.03 (d, J=5.0, 1 OH). $^{13}$C-NMR: 158.5, 146.8, 144.7, 135.9, 135.6, 135.3, 135.2, 135.1 (8s, 10 arom. C), 130.0, 128.1, 127.9, 126.5 (4d, 9 arom. CH), 126.6, 126.4 (2s, 2 arom. C), 125.6, 125.5, 125.2, 125.1, 124.8, 121.6, 121.5, 113.2 (8d, 13 arom. CH), 86.4 (s, 1 C), 84.3, 75.9, 74.9 (3d, H-C(1'), H-C(3'), H-C(4')), 64.5 (t, $H_2$-C(5')), 55.2 (q, 2 $OCH_3$), 42.9 (t, $H_2$-C(2')).

1',2'-Dideoxy-5'-O-(4,4'-dimethoxytrityl)-1'α-[5-(3-thiophen-2-yl-benzo[c]thiophen-1-yl)-thiophen-2-yl]-D-ribofuranose cyanoethyl N,N-diisopropylphosphoramidite (5b, FIG. 2)

According to Procedure D. Reaction was performed under absence of light (flasks wrapped in aluminum foil). 2-Cyanoethyl diisopropylchlorophosphoramidite (166 mg, 0.701 mmol) and DIEA (300 µl, 1.75 mmol) were reacted with 4b, FIG. 2 (318 mg, 0.444 mmol) in 10 ml $CH_2Cl_2$. Purification gave 302 mg 5b, FIG. 2 (0.329 mmol, 74%) as dark yellow foam.

$^1$H-NMR (mixture of 2 diastereoisomers): 7.73–7.67, 7.59–7.25, 6.91–6.87 (3m, 26 arom. H), 5.33, 4.65, 4.43 (3m, H-C(1'), H-C(3'), H-C(4')), 3.84, 3.83 (2s, 2 $OCH_3$), 3.66–3.35, 3.26–3.23 (2m, 2 $NCH(CH_3)_2$, $OCH_2CH_2CN$, 2 H-C(5')), 2.81 (m, 1 H-C(2')), 2.50–2.18 (m, $OCH_2CH_2CN$, 1 H-C(2')), 1.20–1.06 (m, 2 $NCH(CH_3)_2$). $^{13}$C-NMR: 158.4, 144.9, 142.5, 142.2, 140.7, 140.0, 139.9, 139.7, 139.5, 136.1 (10s, 10 arom. C), 130.1, 128.8, 128.3, 127.8, 127.5, 127.40, 127.36, 127.31, 127.0, 126.9, 126.7, 126.5, 126.4 (14d, 22 arom. CH), 117.6, 117.5 (2s, CN), 113.1 (d, 4 arom. CH), 86.1 (s, 1 C), 84.8, 79.9 (2d, H-C(1'), H-C(4')) 75.7, 75.2 (2d, H-C(3')), 64.3, 64.0 (2t, $H_2$-C(5')), 58.3, 58.1 (2t, $OCH_2CH_2CN$), 55.2 (q, 2 $OCH_3$), 43.2, 43.1 (2d, 2 NCH$(CH_3)_2$), 42.5 (t, $H_2$-C(2')), 24.5, 24.4, 24.3 (3q, 2 NCH$(CH_3)_2$), 20.2, 20.1 (2t, $OCH_2CH_2CN$). HRMS calcd. for $C_{53}H_{57}N_2NaO_6P$ ($[M+Na]^+$): 916.2803, found: 916.2831.

EXAMPLE 4

Synthesis of Terphenyl Nucleoside 1',2'-Dideoxy-1'α-[1,1';4',1"]terphenyl-4-yl-3',5'-di-O-toluoyl-D-ribofuranose (2c, FIG. 2)

A solution of 1,2-dibromoethane (2.3 ml, 26.7 mmol) in 50 ml THF was slowly added to a mixture of Mg-turnings (1.131 g, 46.54 mmol) in 100 ml THF at r.t. After addition of about 5 ml of the dibromoethane solution, the Grignard reaction started. 4-Bromo-[1,1';4',1"]terphenyl 1c, FIG. 2 (5.433 g, 17.57 mmol) was added to the reaction mixture (suspension) and the rest of the dibromoethane solution was added slowly during 40 min at 50° C. After stirring for 3 h, $CdCl_2$ (2.213 g, 12.07 mmol) was added to the reaction mixture and it was stirred for 2 h at reflux. Then it was cooled to r.t., a solution of the rs chlorosugar (6.832 g, 17.57 mmol) in 50 ml THF was added and the mixture was stirred for 16 h at r.t. 200 ml $CH_2Cl_2$ were then added to the reaction mixture and it was washed twice with 10% $NH_4Cl$ soln. The aq. layers were extracted with $CH_2Cl_2$/THF 1:1 and the org. layers were dried ($MgSO_4$) and concentrated. Purification by FC (hexane/EtOAc 7:1) gave 2.339 g of 2c, FIG. 2 (4.014 mmol, 23%) as white powder.

$^1$H-NMR: 8.02 (d, J=8.0, 2 arom. H), 7.73–7.66, 7.57–7.48, 7.42–7.39 (3m, 13 arom. H), 7.28, 7.17 (2d, J=8.0, 4 arom. H), 5.66, 5.48 (2m, H-C(1'), H-(3')), 4.77, 4.64 (2m, H-C(4'), 2 H-C(5')), 3.01 (m, H-C(2')), 2.45 (s, MePh), 2.43 (m, H-C(2')), 2.40 (s, MePh). $^{13}$C-NMR: 166.4, 166.1 (2 C=O), 143.9, 143.8, 141.6, 140.6, 140.1, 139.7 (6s, arom. C), 129.7, 129.6, 129.1, 129.0, 128.8, 127.5, 127.4, 127.1, 127.0 (10d, 19 arom. CH) , 126.8 (s, arom. C), 126.1 (d, 2 arom. CH), 82.2, 80.0, 76.4 (3d, H-C(1'), H-C(3'), H-C(4')),64.6, 40.3 (2t, $H_2$-C(5'), $H_2$-C(2')), 21.67, 21.63 (2q, 2 $H_3$CPh). HRMS calcd. for $C_{39}H_{34}O_5$ ($[M]^+$): 582.2406, found: 582.2427.

1',2'-Dideoxy-1'α-[1,1':4',1"]terphenyl-4-yl-D-ribofuranose (3c, FIG. 2)

According to Procedure B. Treatment of 2c, FIG. 2 (427 mg, 0.732 mmol) with 0.5M NaOMe in MeOH (730 µl, 0.365 mmol) in 5 ml MeOH/$CH_2Cl_2$ 1:1 gave 201 mg 3c, FIG. 2 (0.580 mmol, 79%) as white powder.

$^1$H-NMR (THF-$d_8$): 7.70–7.61, 7.48–7.39, 7.33–7.28 (3m, 13 arom. H), 5.05 (m, H-C(1')), 4.37, 4.16, 3.90, 3.82, 3.65, 3.60 (6m, H-C(3'), H-C(4'), 2 H-C(5'), 2 OH)), 2.61, 1.86 (2m, 2 H-C(2')). $^{13}$C-NMR (pyridine-$d_5$): 144.1, 140.9, 140.2, 139.6 (4s, arom. C), 129.4, 127.9, 127.8, 127.3, 127.2, 127.1 (6d, arom. CH), 88.0, 79.8, 73.1 (3d, H-C(1'), H-C(3'), H-C(4')), 63.3, 45.1 (2t, $H_2$-C(5'), $H_2$-C(2')). HRMS calcd. for $C_{23}H_{22}O_3$ ($[M]^+$): 346.1569, found: 346.1553.

1',2'-Dideoxy-5'-O-(4,4'-dimethoxytrityl)-1'α-[1,1';4',1"]terphenyl-4-yl-D-ribofuranose (4c, FIG. 2)

According to Procedure C. DMT-Cl (135 mg, 0.398 mmol), DIEA (70 µl, 0.409 mmol) and a spatula tip of DMAP were added to a solution of 3c (94 mg, 0.271 mmol) in 4 ml pyridine/$CH_2Cl_2$ 1:1 and stirred for 5 h. Purification gave 144 mg 4c, FIG. 2 (0.222 mmol, 82%) as white foam.

$^1$H-NMR: 7.72–7.66, 7.55–7.25 (2m, 22 arom. H), 6.89 (d, J=8.9, 4 arom. H), 5.23 (t, J=7.4, H-C(1')), 4.50, 4.26 (2m, H-C(3'), H-C(4')), 3.83 (s, 2 $OCH_3$), 3.45 (dd, J=9.5, 4.6, H-C(5')), 3.30 (dd, J=9.5, 6.0, H-C(5')), 2.77, 2.12 (2m, 2 H-C(2')). $^{13}$C-NMR: 158.5, 144.8, 142.1, 140.7, 140.1, 139.8, 139.7, 135.9 (8s, 10 arom. C), 130.0, 128.8, 128.1, 127.9, 127.5, 127.4, 127.3, 127.1, 127.0, 126.8, 126.3, 113.2 (12d, 26 arom. CH), 86.4 (s, 1 C), 84.5, 79.5, 75.2 (3d, H-C(1'), H-C(3'), H-C(4')), 64.7 (t, $H_2$-C(5')), 55.2 (q, 2 $OCH_3$), 43.1 (t, $H_2$-C(2')). HRMS calcd. for $C_{44}H_{40}NaO_5$ ($[M+Na]^+$): 671.2773, found: 671.2786.

1',2'-Dideoxy-5'-O-(4,4'-dimethoxytrityl)-1'α-[1,1;4.1',1"]terphenyl-4-yl-D-ribofuranose Cyanoethyl N,N-diisopropylthosihoramidite (5c, FIG. 2)

According to Procedure D. 2-Cyanoethyl diisopropylchlorophosphoramidite (276 mg, 1.166 mmol) and DIEA (500 µl, 2.92 mmol) were reacted with 4c, FIG. 2 (494 mg, 0.761 mmol) in 10 ml $CH_2Cl_2$. Purification gave 554 mg 5c, FIG. 2 (0.652 mmol, 86%) as white foam.

$^1$H-NMR (mixture of 2 diastereoisomers): 7.73–7.67, 7.59–7.25, 6.91–6.87 (3m, 26 arom. H), 5.33, 4.65, 4.43

(3m, H-C(1'), H-C(3'), H-C(4')), 3.84, 3.83 (2s, 2 OCH$_3$), 3.66–3.35, 3.26–3.23 (2m, 2 NCH(CH$_3$)$_2$, OCH$_2$CH$_2$CN, 2 H-C(5')), 2.81 (m, 1 H-C(2')), 2.50–2.18 (m, OCH$_2$CH$_2$CN, 1 H-C(2')), 1.20–1.06 (m, 2 NCH(CH$_3$)$_2$). $^{13}$C-NMR: 158.4, 144.9, 142.5, 142.2, 140.7, 140.0, 139.9, 139.7, 139.5, 136.1 (10s, 10 arom. C), 130.1, 128.8, 128.3, 127.8, 127.5, 127.40, 127.36, 127.31, 127.0, 126.9, 126.7, 126.5, 126.4 (14d, 22 arom. CH), 117.6, 117.5 (2s, CN), 113.1 (d, 4 arom. CH), 86.1 (s, 1 C), 84.8, 79.9 (2d, H-C(1'), H-C(4')) 75.7, 75.2 (2d, H-C(3')), 64.3, 64.0 (2t, H$_2$-C(5')), 58.3, 58.1 (2t, OCH$_2$CH$_2$CN), 55.2 (q, 2 OCH$_3$), 43.2, 43.1 (2d, 2 NCH(CH$_3$)$_2$), 42.5 (t, H$_2$-C(2')), 24.5, 24.4, 24.3 (3q, 2 NCH(CH$_3$)$_2$), 20.2, 20.1 (2t, OCH$_2$CH$_2$CN). HRMS calcd. for C$_{53}$H$_{57}$N$_2$NaO$_6$P ([M+Na]$^+$): 871.3852, found: 871.3846.

EXAMPLE 5

Synthesis of the Stilbene Nucleoside 1',2'-Dideoxy-1'α-(4-styryl-phenyl)-3',5'-di-O-toluoyl-D-ribofuranose (2e, FIG. 2)

A solution of p-bromostilbene (1.444 g, 5.572 mmol) in 25 mL THF was slowly added to Mg turnings (234 mg, 9.63 mmol). After 2 mL of the p-bromostilbene solution was added, iodine crystals and two drops of dibromoethane was added to start the reaction. The rest of the p-bromostilbene was added slowly, then the solution was heated at reflux for 2 hours. To the reaction was added CdCl$_2$ (1.22 g, 6.67 mmol) and heated for another 2 hours at reflux. The reaction was cooled to room temperature and a solution of chloro-sugar (2.731 g, 6.686 mmol) was added slowly via a dropping funnel and stirred for 16 hours. The solution was dried in vacuo to remove the THF. The residue was then dissolved in CH$_2$Cl$_2$ and transferred to a separatory funnel and washed twice with an aqueous solution of saturated NH$_4$Cl. The organic layer was extracted and dried over MgSO$_4$ and concentrated. Purification by FC (hexanes/EtOAc 7:1) gave 2.279g of 2e, FIG. 2 (4.279 mmol, 77%) as a white powder.

$^1$H-NMR: 8.00(d, J=5.1 4H), 7.70 (d J=5.1 2H), 7.54 (m, 3H), 7.42 (m, 3H), 7.28 (m, 5H), 7.27 (m, 2H), 5.42 (m, 1H), 5.40 (t, J=4.2 1H), 4.68 (m, 1H), 4.60 (d, J=4.2 2H), 2.94 (p, J=4.2 1H), 2.44 (s, 3H), 2.42 (s, 3H), 1.62 (s, 1H), 1.28, (t, J=4.5 1H). $^{13}$C-NMR: 144.7, 138.6, 137.1, 129.3 (2s), 128.9, 128.1, 127.2, 127.1, 126.8, 87.6, 80.1, 73.2, 45.3, 25.7, 25.5, 25.3, 25.1, 24.9. HRMS calculated for C$_{35}$H$_{32}$O$_5$ ([M]$^+$): 532.2250, found: 532.3067.

1',2'-Dideoxy-1'α-(4-styryl-phenyl)-D-ribofuranose (3e, FIG. 2)

According to Procedure B. Treatment of 2e, FIG. 2 (203 mg, 0.381 mmol) with 0.5M NaOMe in MeOH (0.76 mL, 0.38 mmol) in 5 mL MeOH/CH$_2$Cl$_2$ 2.5:1 gave 610 mg of 3e, FIG. 2 (2.058 mmol, 75%). $^1$H-NMR: 7.42 (m, 4H), 7.24 (dm, 4H), 7.08 (m, 2H), 4.86 (q, J=4.1 1H), 4.22 (q, J=4.0 1H), 3.70 (q, J=2.7), 3.68 (q, J=2.7), 3.45 (s, 6H), 2.46 (p J=4.1 1H), 1.72 (m, 2H), 1.17 (s, 1H). $^{13}$C-NMR: 166.4, 166.1, 143.9, 143.8, 141.8, 137.3, 136.5, 129.7, 129.6, 129.1, 129.0, 128.7, 128.6, 128.3, 127.6, 127.0, 126.8, 126.5, 126.4, 126.2, 126.0, 82.1, 81.9, 80.0, 76.3, 75.4, 65.1, 64.6, 55.2, 40.3, 39.2, 21.6. HRMS calculated for C$_{19}$H$_{20}$O$_3$ ([M]$^+$): 296.1412, found: 296.1409.

1',2'-Dideoxy-5'-O-(4,4'-dimethoxytrityl)-1'α-(4-styryl-phenyl)-D-ribofuranose (4e, FIG. 2)

According to Procedure C. DMT-Cl (841 mg, 2.46 mmol), DIEA (0.54 mL, 3.09 mmol), and a spatula tip of DMAP were added to a solution of 3e, FIG. 2 (610 mg, 2.058 mmol) in 10 mL of dry pyridine and stirred at room temperature for 4 hours. The reaction mixture was concentrated in vacuo and resulting oil was added directly to column of silica gel that had been pre-equilibrated with 5% TEA in hexanes. Purification by FC (hexanes/EtOAc 6:1 to 1:2) gave 1.037 mg of 4e, FIG. 2 (1.73 mmol, 84%) as a light yellow foam. $^1$H-NMR: 7.54 (m, 6H), 7.45 (m 13 H), 6.88 (s, 2H), 6.86 (s, 2H), 5.16 (t, J=4.6 1 H), 4.46 (p, J=2.9 1H), 4.22 (q, J=3.6 1H), 3.82 (s, 6H), 3.43 (q, J=2.9 1H), 3.27 (dd, J=3.8, 2.1 1H), 2.72 (q, J=3.9 1H), 1.97 (d, 2.8 1H), 1.61 (s, 1H). $^{13}$C-NMR: 158.5, 144.8, 142.3, 137.3, 135.9, 130.0, 128.6, 128.5, 128.3, 128.1, 127.9, 127.6, 126.8, 126.6, 126.4, 126.1, 113.1, 86.3, 84.4, 79.5, 75.2, 64.7, 55.2, 43.0.

1',2'-Dideoxy-5'-O-(4,4'-dimethoxytrityl)-1'α- (4-styryl-phenyl)-D-ribofuranose cyanoethyl N,N-diisopropylphosphoramidite (5e, FIG. 2)

According to Procedure D. 2-Cyanoethyl diisopropyl-chlorophosphoramidite (0.578 mL, 2.59 mmol) and DIEA (1.2 mL, 6.9 mmol) were added to a solution of 4e, FIG. 2 (1.034 mg, 1.727 mmol) in 20 mL CH$_2$Cl$_2$ and stirred at room temperature for 4 hours. Purification by FC (hexanes/EtOAc 3:1) gave 966mg of 5e, FIG. 2 (1.21 mmol, 70%) as a white foam.

$^1$H-NMR: 7.54 (m, 3H), 7.41 (m 7 H), 7.13 (s, 1H), 6.86 (dd, J=1.9, 3.7 2H), 5.16 (t, J=4.6 1 H), 4.60 (dm, 1H), 4.39 (q, J=2.6 1H), 3.81 (s, 6H), 3.52 (m, 2H), 3.29 (m, 4H), 2.85 (m, 1H), 2.20 (m, 1H), 1.59 (s, 2H), 1.15 (m, 6H), 1.11 (d, J=4.2), 1.05 (d, J=4.2). $^{13}$C-NMR: 158.3, 144.8, 142.3, 137.3, 135.9, 130.1, 128.6, 128.5, 128.3, 128.1, 127.9, 127.6, 126.8, 126.6, 126.4, 126.1, 113.0, 86.3, 84.4, 80.0, 75.2, 64.7, 55.1, 42.7, 24.6.

EXAMPLE 6

Synthesis of the Cyclohexene Nucleoside

Besides the set of five fluorophores, a C-nucleoside (3f, FIG. 2) with cyclohexene at the 1-position was prepared for use as a nonfluorescent spacer. Since fluorophores are usually quenched by neighboring DNA bases [21], the cyclohexene compound was designed to be inserted, if desired, between fluorophores and natural DNA bases to possibly limit any quenching that might occur. Cyclohexene was chosen rather than saturated cyclohexane because the former has the same geometry at the point of attachment, as the other subject fluorescent analogs and natural bases.

1',2'-Dideoxy-1'α-cyclohex-1-enyl-3',5'-di-O-toluoyl-D-ribofuranose (2f, FIG. 2)

A solution of 1-bromocyclohexene if (2.090 g, 12.98 mmol) and 1,2-dibromoethane (900 μl, 10.44 mmol) in 40 ml THF was slowly added to Mg-turnings (647 mg, 26.62 mmol) in 10 ml THF. To start the Grignard reaction, the mixture was slightly heated. After complete addition of the bromo compound, the reaction mixture was stirred for 2 h at 50° C. ZnCl$_2$ (901 mg, 6.61 mmol) was added and the mixture was stirred for 2 h at reflux. Then, the reaction was cooled to r.t. and a solution of Hoffer's chlorosugar (5.076 g, 13.05 mmol) in 25 ml THF was added. After stirring for 16 h at r.t., the solvent was evaporated, the residue was suspended in CH$_2$Cl$_2$ and washed twice with 10% NH$_4$Cl soln. The aqueous layers were extracted with CH$_2$Cl$_2$ and the organic layers were dried (MgSO$_4$) and concentrated. Purification by FC (hexanes/EtOAc 6:1) gave 2.313 g 2f, FIG. 2 (5.323 mmol, 41%) as colorless oil which contained about 13% of a double bond isomer as an impurity.

$^1$H-NMR: 7.92 (m, 4 arom. H), 7.22 (m, 4 arom. H), 5.80 (m, 1 H), 5.50 (m, H-C(1')), 4.61, 4.53–4.44 (2m, H-C(3'), H-C(4'), 2 H-C(5')), 2.62 (m, 1 H-C(2')), 2.41, 2.39 (2s, 2 MePh), 2.15–2.01, 1.67–1.54 (2m, 1 H-C(2'), 8 cyclohexene H). $^{13}$C-NMR: 166.3, 166.1 (2 C=O), 143.9, 143.7 (2s, 2 arom. C), 136.7 (s, 1 cyclohexene C), 129.7, 129.6, 129.1, 129.0 (4d, 8 arom. CH), 127.1, 127.0 (2s, 2 arom. C), 123.6 (1d, 1 cyclohexene CH), 82.5, 81.2, 76.3 (3d, H-C(1'), H-C(3'), H-C(4')), 64.7, 36.4 (2t, H$_2$-C(5'), H$_2$-C(2')), 24.9, 23.7, 22.5 (3t, 4 cyclohexene H$_2$-C), 21.6 (q, H$_3$CPh). HRMS calcd. for C$_{27}$H$_{31}$O$_5$ ([M+H]$^+$): 435.2171, found: 435.2185.

1',2'-Dideoxy-1'α-cyclohex-1-enyl-D-ribofuranose (3f, FIG. 2)

According to Procedure B. Treatment of 2f (276 mg, 0.635 mmol) with 0.5M NaOMe in MeOH (630 μl, 0.315 mmol) in 5 ml MeOH/CH$_2$Cl$_2$ 1:1 gave 101 mg 3f, FIG. 2 (0.509 mmol, 80%) as a colorless oil.

$^1$H-NMR: 5.75 (s (br.), 1 cyclohexene H), 4.38, 4.29 (2m, H-C(1'), H-C(3')), 3.83, 3.73, 3.65 (3m, H-C(4'), 2 H-C(5')), 2.92, 2.68 (2s (br.), 2 OH), 2.29 (1m, 1 H-C(21)), 1.96–1.87, 1.67–1.54 (2m, 1 H-C(2'), 8 cyclohexene H-C). $^3$C-NMR: 137.6 (1s, 1 C), 123.5 (1d, 1 H-C), 84.7, 81.7, 72.6 (3d, H-C(1'), H-C(3'), H-C(4')), 62.3, 38.9 (2t, H$_2$-C(5'), H$_2$-C(2')), 24.9, 23.5, 22.4 (3t, 4 cyclohexene H$_2$-C). HRMS calcd. for C$_{11}$H$_{18}$O$_3$: 198.1256, found: 198.1252.

1',2'-Dideoxy-5'-O-(4,4'-dimethoxytrityl)-1'α-cyclohex-1-enyl D-ribofuranose (4f, FIG. 2)

According to Procedure C. DMT-Cl (179 mg, 0.528 mmol), DIEA (150 μl, 0.876 mmol) and a spatula tip of DMAP were added to a solution of 3f, FIG. 2 (85 mg, 0.428 mmol) in 5 ml pyridine/CH$_2$Cl$_2$ 1:1 and stirred for 3 days. Purification gave 182 mg 4f, FIG. 2 (0.363 mmol, 85%) as a colorless oil.

$^1$H-NMR: 7.35 (m, 2 arom. H), 7.25–7.09 (m, 7 arom. H), 6.74 (m, 4 arom. H), 5.67 (m, 1 cyclohexene H), 4.32 (t, J=7.4, H-C(1')), 4.18, 3.91 (2m, H-C(3'), H-C(4')), 3.69 (s, 2 OCH$_3$), 3.23 (dd, J=9.4, 4.6, 1 H-C(5')), 3.03 (dd, J=9.4, 6.4, 1 H-C(5')), 2.21 (m, 1 H-C(2')), 2.11–1.93 (m, 4 cyclohexene H-C), 1.81 (m, 1 H-C(2')), 1.64–1.44 (m, 4 cyclohexene H-C). $^{13}$C-NMR: 158.4, 144.8, 138.1, 136.0 (4s, 5 arom. C, 1 cyclohexene C), 130.0, 128.1, 127.8, 126.7, 122.9, 113.1 (6d, 13 arom. CH, 1 cyclohexene CH), 86.2 (s, 1 C), 83.9, 81.8, 75.1 (3d, H-C(1'), H-C(3'), H-C(4')), 64.9 (t, H$_2$-C(5')), 55.2 (q, 2 OCH$_3$), 40.7 (t, H$_2$-C(2')), 24.9, 23.9, 22.5 (3t, 4 cyclohexene CH$_2$). HRMS calcd. for C$_{32}$H$_{36}$NaO$_5$ ([M+Na]$^+$): 523.2460, found: 523.2480.

1',2'-Dideoxy-5'-O-(4,4'-dimethoxytrityl)-1'α-cyclohex-1-enyl-D-ribofuranose cyanoethyl N,N-diisopropylphosphoramidite (5f, FIG. 2)

According to Procedure D. 2-Cyanoethyl diisopropylchlorophosphoramidite (433 mg, 1.829 mmol) and DIEA (800 μl, 4 mmol) were reacted with 4f, FIG. 2 (586 mg, 1.170 mmol) in 10 ml CH$_2$Cl$_2$. Purification gave 662 mg 5f, FIG. 2 (0.945 mmol, 81%) as white foam.

$^1$H-NMR (mixture of 2 diastereoisomers): 7.53–7.50, 7.42–7.17, 7.09–7.01, 6.93–6.91, 6.86–6.82 (5m, 20 arom. H), 5.43 (m, H-C(1')), 4.57, 4.34 (2m, H-C(3'), H-C(4')), 3.81, 3.80 (2s, 2 OCH$_3$), 3.72–3.48, 3.38–3.27, 3.17–3.13 (3m, 2 NCH(CH$_3$)$_2$, OCH$_2$CH$_2$CN, 2 H-C(5')), 2.75 (m, 1 H-C(2')), 2.56–2.51 (m, OCH$_2$CH$_2$CN), 2.37 (m, 1 H-C(2')), 1.17–1.03 (m, 2 NCH(CH$_3$)$_2$). $^{13}$C-NMR: 158.4, 146.1, 144.9, 137.1, 136.4, 136.1, 136.0 (7s, 10 arom. C), 130.1, 128.2, 127.9, 127.8, 126.7, 124.9, 124.4, 124.3, 124.0, 123.6, 123.2 (11d, 16 arom. CH), 117.5 (s, CN), 113.1 (d, 4 arom. CH), 86.1 (s, 1 C), 84.7, 76.3 (2d, H-C(1'), H-C(4')) 75.0, 74.8 (2d, H-C(3')), 63.8 (t, H$_2$-C(5')), 58.2, 58.1 (2t, OCH$_2$CH$_2$CN), 55.2 (q, 2 OCH$_3$), 43.2, 43.1 (2d, 2 NCH (CH$_3$)$_2$), 42.4 (t, H$_2$-C(2')), 24.6, 24.5, 24.4, 24.3 (4q, 2 NCH(CH$_3$)$_2$), 20.1, 20.0 (2t, OCH$_2$CH$_2$CN). HRMS calcd. for C$_{41}$H$_{53}$N$_2$NaO$_6$P [M+Na]$^+$: 723.3539, found: 723.3528.

EXAMPLE 7

Absorption/Emission Spectra and Auantum Yields

Absorption and emission spectra of 10 μM solutions of the deprotected nucleosides (3a,b,c,e, FIG. 2) and of the earlier described pyrene nucleoside 3d, FIG. 2 were measured in deoxygenated methanol at room temperature on a Cary I UV/VIS-spectrometer. Excitation spectra were also measured at the emission maxima, and the spectra were identical to the absorption curves shown in FIG. 4. The quantum yields were also determined for the five compounds (Table 1) using quinine sulfate and fluorescein as standards. The results, depicted in FIG. 4, show absorption maxima ranging from 285 nm for the terphenyl-derivatized nucleoside to 437 nm for benzoterthiophene derivatized nucleoside, which appears yellow-orange in solution under incandescent light. Emission maxima range from 345 nm for terphenyl (3c, FIG. 2) (a violet-blue fluorophore) to 536 nm for the benzoterthiophene derivative (3b, FIG. 2) which fluoresces bright yellow.

Not surprisingly, there is little difference in the absorbance and fluorescence spectra of the nucleoside analogs (3a–e, FIG. 2) depicted as and the corresponding free fluorophores. The quantum yields of the terthiophene nucleoside (3a, FIG. 2) and free terthiophene (6, FIG. 3) are about the same as the reported quantum yield for free terthiophene [27], and the quantum yield of pyrene nucleoside (3d, FIG. 2) is similar that of 1-pyrenebutyric acid. The quantum yield measured is about 20-fold smaller than the quantum yield reported by Telser et al. [28] for pyrenebutyrate. Telser et al. used a different value for the quantum yield of quinine sulfate (0.70 instead of 0.55) and measured the quantum yield in an aqueous buffer. The sharpness of the absorption and emission lines for this compound may have caused difficulties in accurately measuring a maximum value. The quantum yield measured for the stilbene nucleoside (3e, FIG. 2) is about 50% smaller than the quantum yield reported by Lewis et al. [29] for a stilbene dicarboxamide at the excitation wavelength of 330 nm, which was determined in a 4:1 aqueous ethanol solution, using a phenanthrene standard.

Fluorescence spectra of 10 μM solutions in methanol (except terthiophene 7, FIG. 3 in CH$_2$Cl$_2$) were measured on a SPEX 1680 Double Spectrometer at room temperature. The solvents were deoxygenated by bubbling nitrogen through the solvent for 2 hours. The spectra were corrected for instrument response. All slits were set to 2 mm, resulting in ~3.4 nm resolution. Fluorescence quantum yields ($\Phi_f$) were calculated by the equation:

$$\Phi_f = \frac{FA_s\eta^2\Phi_s}{AF_s\eta_0^2}$$

where the subscript s refers to the standard, $\Phi_f$ is the quantum yield, F is the corrected, integrated fluorescence, A is the absorption at the excitation wavelength, $\eta$ is the refractive index of methanol (or CH$_2$Cl$_2$) and $\eta_0$ is the refractive index of water [30]. As quantum yield standards were used quinine sulfate (Aldrich, 99+%, used without further purification), 10 μM in 1N H$_2$SO$_4$ ($\Phi_f$=0.55 [31, 32]) and fluorescein (Aldrich, recrystallized from 1N NaOH by adding 10% acetic acid), 10 μM in 0.1N NaOH ($\Phi_f$=0.90 [31]).

TABLE 1

Absorption and Emission Data and Quantum Yields ($\Phi_f$) for Nucleosides 3a-e of FIG. 1 in Methanol.

| | absorption maxima (nm) | extinction coeff. (M$^{-1}$ cm$^{-1}$) | emission maxima (nm) | $\Phi_f$ (excitation, nm) |
|---|---|---|---|---|
| 3a | 358 | 31,400 | 432 | 0.059 (358) |
| 3b | 437 | 18,300 | 536 | 0.67 (440) |
| 3c | 285 | 40,100 | 345 | 0.42 (290) |
| 3d | 343 | 34,400 | 377 | 0.025 (344) |
| 3e | 301 | 21,100 | 356 | 0.055 (298) |
| 1-pyrenebutyric acid | 343 | 33,800 | 377 | 0.027 (344) |
| terthiophene[a] | 355 | 29,900 | 431 | 0.063 (358)[b] |

[a]Methylene chloride solvent.
[b]The reported quantum yield is 0.055 [27]

EXAMPLE 8

FRET Between More than Two Dyes

A DNA strand was synthesized having two pyrene residues at directly adjacent nucleotide positions. The presence of the two pyrene residues resulted in intense excimer fluoresence, indicating interaction of the two pyrene residues. A second oligonucleotide containing a rhodamine dye was hybridized to the DNA strand. The resulting fluorescence spectrum was then measured with excitation at 341 nm. 341 nm is known to excite pyrene but not rhodamine. Binding of the two oligonucleotides was found to result in significant levels of rhodamine emission (630 nm) with a simultaneous decrease in pyrene excimer emission. These results indicate that energy transfer occurs first between the two pyrene molecules and then to a rhodamine dye. The overall Stokes shift of this energy transfer is greater than 275 nm. Since pyrene excimer emission occurs with a very broad emission band, these results indicate that many different available dyes could act as acceptors in designing fluorescently labeled nucleic acids.

EXAMPLE 9

Construction of a Combinatorial Fluorphore Array Library

A combinatorial fluorophore array (CFA) library was constructed using stilbene, pyrene, terphenyl and terthiophene as nucleoside analogs. The nucleoside analogs were continuously incorporated into a 5 nucleotide long sequence yielding a total diversity of 1,024 (4$^5$) total fluorophore array sequences. The sequences were placed on the beads at each step using the method of Ohlmeyer M. H., et al. (1993), synthesized on Tentagel beads.

The beads were visualized both by eye and over a transilluminator and also under a fluorescence microscope. The labeled sequences emitted colors ranging from violet to blue to green to green-yellow.

EXAMPLE 10

Selecting for a Change in Fluorescence on Binding an Analyte

A combinatorial fluorophore array is constructed on Tentagel beads, incorporating nucleoside analogs such as pyrene, stilbene, terthiophene, terphenyl, and benzoterthiophene into a sequence six units long, using split and pool methods. After that step, a DNA sequence is added to the end of all libraries on the beads. This DNA sequence is known to have affinity for the protein TGF-beta (transforming growth factor beta).

An analyte solution containing TGF-beta is then washed over the beads while monitoring them under the fluorescence microscope with digital imaging. Most beads do not change. However, some beads are observed to lower their fluorescence signal in the presence of the analyte, while some increase their signal. A few are observed to alter their color (such as from blue to green). These latter beads are removed one at a time and are analyzed for their sequence of fluorophores. It is found that a specific sequence of six fluorophores (connected to the affinity DNA) leads to this color change. This same sequence of fluorophores attached to the TGF-beta affinity DNA is then constructed in pure form using standard DNA synthesis methods and is placed in solution. Addition of an analyte containing TGF-beta results in a dramatic, easily visualized color change. This molecule thus acts as a fluorescent sensor of TGF-beta, and can be used in solution, on DNA chips and microarrays, and in situ.

REFERENCES

[1]
(a) C. A. Royer, *Methods Mol. Biol.* 1995, 40, 65;
(b) P. Wu, L. Brand, *Anal. Biochem.* 1994, 218, 1.
[2]
(a) A. Holzwarth, *Methods Enzymol.* 1995, 246, 334;
(b) D. P. Millar, *Curr. Opin. Struct. Biol.* 1996, 6, 637.
[3]
(a) S. L. Beaucage, R. P. Iyer, *Tetrahedron* 1993, 49, 1925;
(b) R. E. Cunningham, *Methods Mol. Biol.* 1999, 115, 271.
[4]
(a) T. Heyduk, Y. Ma, H. Tang, R. H. Ebright, *Methods Enzymol.* 1996, 274, 492;
(b) J. R. Lundblad, M. Laurance, R. H. Goodman, *Mol. Endocrinol.* 1996, 10, 607.
[5]
(a) J. R. Barrio, J. A. Secrist III, N. J. Leonard, *Biochem. Biophys. Res. Commun.* 1972, 46, 597;
(b) S. C. Srivastava, S. K. Raza, R. Misra, *Nucleic Acids Res.* 1994, 22, 1296.
[6] D. C. Ward, E. Reich, L. Stryer, *J. Biol. Chem.* 1969, 244, 1228.
[7] B. W. Allan, N. O. Reich, J. M. Beechem, *Biochemistry* 1999, 38, 5308.
[8] M. R. Otto, L. B. Bloom, M. F. Goodman, J. M. Beechem, *Biochemistry* 1998, 37, 10156.
[9] W. Bujalowski, M. M. Klonowska, *Biochemistry* 1994, 33, 4682.
[10] R. X. F. Ren, N. C. Chaudhuri, P. L. Paris, S. Rumney, E. T. Kool, *J. Am. Chem. Soc.* 1996, 118, 7671.
[11] S. Moran, R. X.-F. Ren, C. J. Sheils, S. Rumney, E. T. Kool, *Nucleic Acids Res.* 1996, 24, 2044.
[12] R. S. Coleman, M. L. Madaras, *J. Org. Chem.* 1998, 63, 5700.
[13] J. P. Erzberger, D. Barsky, O. D. Scharer, M. E. Colvin, D. M. Wilson, *Nucleic Acids Res.* 1998, 26, 2771.
[14] P. L. Paris, J. M. Langenhan, E. T. Kool, *Nucleic Acids Res.* 1998, 26, 3789.
[15] K. M. Guckian, B. A. Schweitzer, R. X. F. Ren, C. J. Sheils, P. L. Paris, D. C. Tahmassebi, E. T. Kool, *J. Am. Chem. Soc.* 1996, 118, 8182.

[16] T. J. Matray, E. T. Kool, *J. Am. Chem. Soc.* 1998, 120, 6191.
[17] T. J. Matray, E. T. Kool, *Nature* 1999, 399, 704.
[18] N. C. Chaudhuri, E. T. Kool, *Tetrahedron Lett.* 1995, 36, 1795.
[19] N. C. Chaudhuri, R. X. F. Ren, E. T. Kool, *Synlett* 1997, 341.
[20] F. Morvan, B. Rayner, J.-L. Imbach, *Anticancer Drug Des.* 1991, 6, 521.
[21] M. Manoharan, K. L. Tivel, M. Zhao, K. Nafisi, T. L. Netzel, *J. Phys. Chem.* 1995, 99, 17461.
[22] A. K. Mohanakrishnan, M. V. Lakshmikantham, C. McDougal, M. P. Cava, J. W. Baldwin, R. M. Metzger, *J. Org. Chem.* 1998, 63, 3105.
[23]
   a) A. McKillop, D. Bromley, E. C. Taylor, *J. Org. Chem.* 1972, 37, 88.
   b) R. Rossi, A. Carpita, M. Ciofalo, V. Lippolis, *Tetrahedron* 1991, 39, 8443.
   c) P. Bäuerle, F. Wurthner, G. Götz, F. Effenberger, *Synthesis* 1993, 1099.
[24] L. Cardona, I. Fernandez, B. Garcia, J. R. Pedro, *Tetrahedron* 1986, 42, 2725.
[25] G. Ndebeka, S. Raynal, P. Caubere, *J. Org. Chem.* 1980, 45, 5394.
[26] M. Hoffer, *Chem. Ber.* 1960, 93, 2777.
[27] P. Garcia, J. M. Pernaut, P. Hapiot, V. Wintgens, P. Valat, F. Garnier, D. Delabouglise, *J. Phys. Chem.* 1993, 97, 513.
[28] J. Telser, K. A. Cruickshank, L. E. Morrison, T. L. Netzel, *J. Am. Chem. Soc.* 1989, 111, 6966.
[29] F. D. Lewis, T. F. Wu, E. L. Burch, D. M. Bassani, J. S. Yang, S. Schneider, W. Jager, R. L. Letsinger, *J. Am. Chem. Soc.* 1995, 117, 8785.
[30] D. J. Simpson, C. J. Unkefer, T. W. Whaley, B. L. Marrone, *J. Org. Chem.* 1991, 56, 5391.
[31] J. N. Demas, G. A. Crosby, *J. Phys. Chem.* 1971, 75, 991.
[32] J. Olmsted, *J. Phys. Chem.* 1979, 83, 2581.

What is claimed is:

1. A nucleoside analog in which a fluorescent cyclic compound is joined to a carbon of a sugar moiety in either an α or β configuration wherein said sugar moiety is pentose or hexose, and wherein the fluorescent cyclic compound is joined to the C1 position of the sugar moiety and wherein said fluorescent cyclic compound is p-terphenyl, perylene, perylene amide, perylene imide, azobenzene, phenazine, phenanthroline, acridine, thioxanthrene, chrysene, rubrene, coronene, cyanine, or an oligomer of varying length selected from the group consisting of oligo(phenylene acetylene), oligothiophene, and oligobenzothiophene.

2. The nucleoside analog of claim 1 wherein the fluorescent cyclic compound is an oligomer of varying length which is oligo(phenylene acetylene).

3. The nucleoside analog of claim 2 wherein the fluorescent cyclic compound has an oligomer length of from about 1 to about 16.

4. The nucleoside analog of claim 1 wherein the oligothiophene is a terthiophene or a sexithiophene.

5. The nucleoside analog of claim 1 wherein the oligobenzothiophene is a benzoterthiophene or a terbenzothiophene.

6. A nucleoside analog in which a fluorescent cyclic compound joined to a carbon of a sugar moiety is in either an α or β configuration wherein said sugar moiety is pentose or hexose, and wherein the fluorescent cyclic compound is joined to the C-1 position of the sugar moiety, said fluorescent compound being styrylstilbene.

7. The nucleoside analog of claim 2 wherein the oligo (phenylene acetylene) is diphenylacetylene or phenyl (ethynyl)diphenylacetylene.

8. The nucleoside analog of claim 1 wherein the fluoescent cyclic compound is selected from the group consisting of p-terphenyl, perylene, azobenzene, phenazine, phenanthroline, acridine, thioxanthrene, chrysene, rubrene, coronene, cyanine, perylene imide, and perylene amide.

9. A nucleoside analog in which a non-fluorescent cyclic compound is joined to a carbon of a sugar molecule, wherein said sugar molecule is pentose or hexose, wherein the cyclic compound is cyclohexane, decalin, benzene or dimethylaminobenzene, and wherein the cyclic compound is joined to the C1 position of the sugar moiety.

10. A nucleoside analog according to any one of claims 1–9 wherein the nucleoside analog is derivatized at an available carbon position with a substituent selected from the group consisting of methoxy, ethoxy, alkoxy, alkyl, dimethylamino, diethylamino, nitro, methyl, cyano, carboxy, fluoro, chloro, bromo, iodo and amino.

11. A nucleic acid molecule comprising at least one nucleoside analog according to any one of claims 1–9.

12. A nucleic acid molecule comprising at least one nucleoside analog according to claim 10.

13. An oligomer comprising nucleoside analogs of any one of claims 1–9.

14. An oligomer comprising nucleoside analogs according to claim 10.

15. A phosphoramnidite derivative of a nucleoside analog of any one of claims 1–9 wherein the phosphoramidite is joined to the sugar moiety at the 3' position.

16. A phosphoramidite derivative of a nucleoside analog of claim 10 wherein the phosphoramidite is joined to the sugar moiety at the 3' position.

17. The phosphoramidite derivative of claim 15 wherein the phosphoramidite derivative is N,N-diisopropyl-O-cyanoethyl phosphoramidite or O-methyl-phosphoramidite derivatized at the 3' alcohol of the nucleoside analog.

18. The phosphoramidite derivative of claim 16 wherein the phosphoramidite derivative is N,N-diisopropyl-O-cyanoethyl phosphoramidite or O-methyl-phosphoramidite derivatized at the 3' alcohol of the nucleoside analog.

19. A nucleoside 5'-3'-paratoluoyl diester derivatized at a carbon atom of a sugar moiety with a fluorescent cyclic compound of any one of claims 1–9.

20. A nucleoside 5'-3'-paratoluoyl diester derivatized at a carbon atom of a sugar moiety with the fluorescent cyclic compound of claim 10.

21. A method of synthesizing the nucleoside analog of claim 1 which comprises:
   a. coupling an organocadmium or organozinc derivative of a fluorescent cyclic compound to a carbon of Hoffer's α-chlorosugar; and
   b. removing the protecting groups with a methanolic base.

22. A method of synthesizing the nucleoside analog of claim 2 which comprises:
   a. coupling an organocadmium or organozinc derivative of any one of oligothiophene, oligobenzothiophene, oligo (phenylene vinylene) or oligo (phenylene acetylene) to a carbon of Hoffer's α-chlorosugar; and
   b. removing the protecting groups with a methanolic base.

23. A method of synthesizing the nucleoside analog of claim 8 which comprises:
   a. coupling an organocadmium or organozinc derivative of any one of p-terphenyl, perylene, dimethylamino benzene, azobenzene, phenazine, napthalene, phenanthroline, acridine, thioxanthrene, chrysene, rubrene, coronene, cyanine, perylene imide, or perylene amide to a carbon of Hoffer's α-chlorosugar; and b. removing the protecting groups with a methanolic base.

24. A method of synthesizing a phosphoramidite derivative of the nucleoside analog of any one of claims 1–8 which comprises:

a. coupling an organocadmium or organozinc derivative of a fluorescent cyclic compound of any one of claims 1 or 3–9 of a carbon of Hoffer's α-chlorosugar;

b. removing the protecting groups with a methanolic base;

c. tritilating the 5'-OH with dimeoxytritylchloride in the presence of a base; and d. phosphytilating the 3'-OH with a phosphitylating agent.

25. A method of synthesizing the nucleoside analog of claim 9 which comprises:

a. coupling an organocadmium or organozinc derivative of any one of cyclohexane, cylclohexene, decalin or benzene to a carbon position of Hoffer's α-chlorosugar; and b. removing the protecting groups with a methanolic base.

26. A method of synthesizing a phosphoramidite derivative of a nucleoside analog comprising a non-fluorescent cyclic compound joined to a carbon of a sugar molecule, wherein said sugar molecule is a pentose or hexose, wherein the cyclic compound is cyclohexane, decalin, benzene or dimethylaminobenzene, and wherein the cyclic compound is joined to the C1 position of the sugar moiety, which method comprises:

a. coupling an organocadmium or organozinc derivative of a fluorescent cyclic compound of claim 9 to a carbon of Hoffer's α-chlorosugar;

b. removing the protecting groups with a methanolic base;

c. tritilating the 5'-OH with dimethytritylchloride in the presence of a base; and d. phosphytilating the 3'-OH with a phosphytilating agent.

27. A method of preparing a fluorescently labeled nucleic acid molecule which comprises incorporating at least one nucleoside analog of any one of claims 1–8 into an RNA or DNA molecule under conditions sufficient to incorporate said nucleoside.

28. A method of detecting a target nucleic acid in a sample to be tested which comprises contacting the target nucleic acid with a nucleic acid probe comprising at least one nucleoside analog of any one of claims 1–8 for a time and under conditions sufficient to permit hybridization between said target and said probe; and detecting said hybridization.

29. A combinatorial fluorophore array (CFA) library which comprises multiple solid supports or multiple locations on a solid support, wherein each support or location has attached thereto an oligomer comprising the fluorescent nucleoside analog comprising a fluorescent cyclic compound joined to a carbon of a sugar moiety in either an α- or β configuration wherein said sugar moiety is a pentose or hexose, and wherein the fluorescent cyclic compound is joined to the C-1 position of the sugar moiety.

30. The combinatorial fluorophore array (CFA) library of claim 29 further comprising one or more unlabeled nucleosides wherein the one or more unlabeled nucleosides are positioned 5' or 3' to the fluorescent nucleoside analogs or interspaced between the fluorescent nucleoside analogs.

31. The CFA library of any one of claim 29, further comprising one or more non-fluorescent nucleoside analogs selected from the group consisting of cyclohexene-2-deoxyriboside, cyclohexane-2-deoxyriboside, decalin-2-deoxyriboside, and benzene-2-deoxyriboside wherein said one or more non-fluorescent nucleotide analogs is interspaced between the fluorescent nucleotide analogs.

32. The CFA library of claim 30 further comprising one or more non-fluorescent nucleoside analogs selected from the group consisting of cyclohexene-2-deoxyriboside, cyclohexane-2-deoxyriboside, decalin-2-deoxyriboside, and benzene-2-deoxyriboside wherein said one or more non-fluorescent nucleoside analogs is interspaced between the fluorescent nucleoside analogs or between the fluorescent nucleoside analogs and the and unlabeled nucleosides.

33. An oligonucleotide analog comprising one or more nucleoside analogs of any one of claims 1–9 in place of a DNA or RNA base.

34. An oligonucleotide analog comprising one or more nucleoside analogs of claim 10 in place of a DNA or RNA base.

35. The oligonucleotide analog of claim 33 in which the sugar-phosphate backbone is modified.

36. The oligonucleotide analog of claim 34 in which the sugar-phosphate backbone is modified.

37. The oligonucleotide analog of claim 35 which is phosphorothioate DNA, 2'-O-methyl RNA, phosphoramidite DNA, 2'fluoro DNA, peptide nucleic acid (PNA) or alpha DNA.

38. The oligonucleotide analog of claim 36 which is phosphorothioate DNA, 2'-O-methyl RNA, phosphoramidite DNA, 2'fluoro DNA, peptide nucleic acid (PNA) or alpha DNA.

39. The combinatorial fluorophore array (CFA) library of claim 29 wherein the fluorescent cyclic compound is an oligomer of varying length selected from the group consisting of oligothiophene, oligobenzothiophene, oligo (phenylene vinylene), and oligo(phenylene acetylene).

40. The combinatorial fluorophore array (CFA) library of claim 39 wherein the fluorescent cyclic compound has an oligomer length of from about 1 to about 16.

41. The combinatorial fluorophore array (CFA) library of claim 39 wherein the oligothiophene is a terthiophene or a sexithiophene.

42. The combinatorial fluorophore (CFA) library of claim 39 wherein the oligobenzothiophene is a benzoterthiophene or a terbenzothiophene.

43. The combinatorial fluorophore (CFA) library of claim 39 wherein the oligo(phenylene vinylene) is dimethylamino stilbene or styrylstilbene.

44. The combinatorial fluorophore (CFA) library of claim 39 wherein the oligo(phenylene acetylene) is diphenylacetylene or phenyl(ethynyl)diphenylacetylene.

45. The combinatorial fluorophore (CFA) library of claim 39 wherein the fluorescent cyclic compound is selected from the group consisting of p-terplienyl, perylene, azobenzene, phenazine, napthalene, phenanthroline, acridine, thioxanthrene, chrysene, rubrene, coronene, cyanine, perylene imide, and perylene amide.

46. The nucleoside analog according to claim 1 wherein the pentose is ribose or deoxyribose.

47. The nucleoside analog according to claim 9 wherein the pentose is ribose or deoxyribose.

48. The combinatorial fluorophore library of claim 29 wherein pentose is ribose or deoxyribose.

* * * * *